US012790342B2

(12) United States Patent
Dan et al.

(10) Patent No.: US 12,790,342 B2
(45) Date of Patent: Nov. 10, 2026

(54) PHARMACEUTICALLY ACCEPTABLE SALT OF MOR RECEPTOR AGONIST, AND POLYMORPH THEREOF AND USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Taizhou (CN)

(72) Inventors: Zhaoling Dan, Shanghai (CN); Taotao Jiang, Shanghai (CN); Jibiao Wang, Shanghai (CN); Jinlei Qiang, Shanghai (CN)

(73) Assignees: Shanghai Haiyan Pharmaceutical Technology Co., Ltd., Shanghai (CN); Yangtze River Pharmaceutical Group Co., Ltd., Taizhou (CN)

( * ) Notice: Subject to any disclaimer, the term of this patent is extended or adjusted under 35 U.S.C. 154(b) by 343 days.

(21) Appl. No.: 18/579,213

(22) PCT Filed: Jul. 13, 2022

(86) PCT No.: PCT/CN2022/105473

§ 371 (c)(1),
(2) Date: Jan. 12, 2024

(87) PCT Pub. No.: WO2023/284788

PCT Pub. Date: Jan. 19, 2023

(65) Prior Publication Data

US 2024/0317761 A1 Sep. 26, 2024

(30) Foreign Application Priority Data

Jul. 13, 2021 (CN) ......................... 202110788712.4

(51) Int. Cl.

| | |
|---|---|
| ***C07D 487/04*** | (2006.01) |
| ***A61K 31/4439*** | (2006.01) |
| ***C07C 55/10*** | (2006.01) |
| ***C07C 57/145*** | (2006.01) |
| ***C07C 59/255*** | (2006.01) |

(52) U.S. Cl.

CPC ........ *C07D 487/04* (2013.01); *A61K 31/4439* (2013.01); *C07C 55/10* (2013.01); *C07C 57/145* (2013.01); *C07C 59/255* (2013.01)

(58) Field of Classification Search

CPC .. C07D 487/04; A61K 31/4439; C07C 55/10; C07C 57/145; C07C 59/255; C07C 55/08; A61P 1/04; A61P 29/00; A61P 9/00; A61P 11/00; A61P 13/00; A61P 25/00; A61P 37/00; C07B 2200/13

See application file for complete search history.

(56) References Cited

U.S. PATENT DOCUMENTS

| | | | | |
|---|---|---|---|---|
| 12,540,138 | B2 * | 2/2026 | Hu | A61P 29/00 |
| 12,545,680 | B2 * | 2/2026 | Hu | A61P 1/04 |
| 2018/0297988 | A1 | 10/2018 | Li et al. | |
| 2019/0343819 | A1 | 11/2019 | Yamashita et al. | |
| 2023/0128062 | A1 * | 4/2023 | Hu | A61P 1/04 514/338 |

FOREIGN PATENT DOCUMENTS

| | | | | |
|---|---|---|---|---|
| CN | 108366997 | A | 8/2018 | |
| CN | 109206417 | A | 1/2019 | |
| CN | 109516982 | A | 3/2019 | |
| CN | 111662284 | A | 9/2020 | |
| EP | 4265604 | A1 | 10/2023 | |
| JP | 2018534257 | A | 11/2018 | |
| JP | 2020534294 | A | 11/2020 | |
| JP | 2020535177 | A | 12/2020 | |
| JP | 2024501554 | A | 1/2024 | |
| WO | WO2011027081 | A2 | 3/2011 | |
| WO | WO2012129495 | A1 | 9/2012 | |
| WO | WO2014041349 | A1 | 3/2014 | |
| WO | WO2017063509 | A1 | 4/2017 | |
| WO | WO2017106547 | A1 | 6/2017 | |
| WO | WO2018188641 | A1 | 10/2018 | |
| WO | WO2018188643 | A1 | 10/2018 | |
| WO | WO2019144805 | A1 | 8/2019 | |
| WO | WO2019205983 | A1 | 10/2019 | |
| WO | WO-2021143801 | A1 * | 7/2021 | A61P 1/04 |

(Continued)

OTHER PUBLICATIONS

Stahl et al. (Handbook of Pharmaceutical Salts, 2002, 1-374). (Year: 2002).*

Office Action for Australian Application No. 2022312049, Dated Oct. 31, 2024, 3 pages.

Caira, "Crystalline Polymorphism of Organic Compounds," Topics in Current Chemistry, vol. 198, 1998, pp. 163-208.

Gupta, et al, "Salts of Therapeutic Agents: Chemical Physicochemical, and Biological Considerations," Molecules, vol. 23, No. 1719, 2018, 15 pages.

Office Action for Japanese Application No. 2024-502238, Dated Jan. 14, 2025, 6 pages.

Office Action for Russian Application No. 2024103448/04(007602), Dated Aug. 29, 2024, 29 pages.

(Continued)

*Primary Examiner* — Rebecca L Anderson
*Assistant Examiner* — Meghan C Heasley
(74) *Attorney, Agent, or Firm* — Lee & Hayes, P.C.

(57) ABSTRACT

Disclosed are a pharmaceutically acceptable salt of an MOR receptor agonist, and a polymorph thereof and the use thereof. Specifically, disclosed are a pharmaceutically acceptable salt of (4S,6S)-6-isopropyl-N-(2-((R)-9-(pyridin-2yl)-6-oxa spiro[4.5]decyl-9-yl)ethyl)-5,6-dihydro-4H-pyrrolo[1,2-b]pyrazol-4-amine, and a polymorph thereof and the use thereof. In addition, further disclosed are a pharmaceutical composition containing the pharmaceutically acceptable salt of the compound or the polymorph thereof, and the use thereof.

14 Claims, 8 Drawing Sheets

(56) References Cited

FOREIGN PATENT DOCUMENTS

| | | | | | |
|---|---|---|---|---|---|
| WO | WO-2021143803 | A1 * | 7/2021 | | A61P 29/00 |
| WO | WO2022143715 | A1 | 7/2022 | | |

OTHER PUBLICATIONS

Sarma, et al., "Solid Forms of Pharmaceuticals: Polymorphs, Salts, and Cocrystals," Korean J. Chem. Eng., vol. 28, No. 2, 2011, pp. 315-322.

Variankaval, et al., "From Form to Function: Crystallization of Active Pharmaceutical Ingredients ," AlChE Journal, vol. 54, No. 7, Jul. 2008, pp. 1682-1688.

International Search Report and Written Opinion mailed Oct. 10, 2022 in International Application No. PCT/CN2022/105473, 16 pages.

Search Report for European Application No. 22841421.5, Dated May 19, 2025, 10 pages.

Notice of Allowance for Korean Application No. KR10-2024-7004602, Dated Apr. 3, 2026, 10 pages.

Larsen, Scott, "Novel Parham-Type Cycloacylations of 1H-Pyrazole-1-Alkanoic Acids," Synlett, vol. 8, Aug. 1997, pp. 1013-1014.

* cited by examiner

PHARMACEUTICALLY ACCEPTABLE SALT OF MOR RECEPTOR AGONIST, AND POLYMORPH THEREOF AND USE THEREOF

CROSS REFERENCES TO RELATED APPLICATIONS

This application is a U.S. National Phase of International Application No. PCT/CN2022/105473, filed Jul. 13, 2022, which claims the priority of a Chinese Patent Application No. 202110788712.4, filed with the China National Intellectual Property Administration on Jul. 13, 2021, and entitled "PHARMACEUTICALLY ACCEPTABLE SALT OF MOR RECEPTOR AGONIST, AND POLYMORPH THEREOF AND USE THEREOF", the entire content of both of which are is-incorporated by reference herein.

TECHNICAL FIELD

The present disclosure belongs to the technical field of medical technology, in particular, it relates to pharmaceutically acceptable salt of an MOR receptor agonist, polymorph thereof, and use thereof.

BACKGROUND

Opioid receptors are a class of important G-protein coupled receptors (GPCR), which are binding targets of the endogenous opioid peptides and opioids drugs. Endogenous opioid peptides are naturally produced opioid-like active substances in mammals. The currently known endogenous opioid peptides are roughly divided into enkephalins, endorphins, dynorphins, and neorphins. Corresponding opioid receptors are present in the central nervous system, including the μ(MOR), δ(DOR), κ(KOR) receptors, etc. Studies have shown that the strength of the analgesic effect of endogenous opioid peptide depends mainly on the expression of opioid receptors, which are the targets of opioid drugs and endogenous opioid peptide for analgesia.

Current research suggests that GPCR mediates and regulates physiological functions mainly through two pathways: the G protein pathway and the β-arrestin pathway. Upon traditional GPCR agonists bind to the receptors, they activate the G-protein signaling pathway, including second messenger system such as calcium ions, adenyl cyclase (AC), mitogen-activated protein kinases (MAPK) and so on, while β-arrestin preferential ligands mainly activate the β-arrestin pathway. The β-arrestin mediated GPCR reaction includes three aspects: 1) as a negative regulatory factor, interacting with G protein-coupled receptor kinase (GRK) to cause receptor desensitization of GPCRs and stop G protein signaling; 2) as a scaffold protein, recruiting endocytic proteins, and inducing GPCR endocytosis; 3) as linker proteins, forming a complex with downstream signaling molecules of GPCR and activating signal transduction molecules in a G-protein independent manner, such as MAPK, Src protein tyrosine kinases, and Akt, among others. Differences in ligand-stimulated G-protein signaling and/or β-arrestin signaling ultimately determine the ligand-specific cellular biological effects of GPCR.

MOR is the target of endogenous enkephalins and opioid analgesics such as morphine. Early studies showed that endogenous enkephalins and the opioid drug etorphine can stimulate the G protein and induce receptor endocytosis, but morphine does not induce receptor endocytosis at all, because morphine has too little ability to stimulate MOR phosphorylation and only can recruit trace amounts of β-arrestin on the membrane (Zhang et al. Proc Natl Acad Sci USA, 1998, 95(12):7157-7162). Such ligands exert their physiological functions entirely through the G protein signaling pathway rather than the β-arrestin pathway. Studies have shown that the analgesic effect mediated by G protein signaling is stronger and lasts longer after morphine injection in β-arrestin2 knockout mice (Bohn et al. Science, 1999). It can be seen that if such ligands have a stronger negative β-arrestin preference and can even escape β-arrestin-mediated receptor desensitization, this may lead to a longer G-protein signaling and a more potent analgesic effect.

At present, the published patent applications for MOR agonists include WO2017106547, WO2017063509, WO2012129495, WO2017106306, and the like.

Long-term use of opioid drugs will produce side effects such as tolerance, respiratory depression, and constipation, which have been proved to be closely related to the function of β-arrestin. In order to reduce the side effects of opioid drugs can be designed based on the negative β-arrestin-preferred ligands of MOR to reduce the side effects mediated by β-arrestin and enhance therapeutic efficacy.

In view of the above-mentioned background in case that the developed MOR receptor agonists had poor properties of the free base, it is necessary to further develop the pharmaceutically acceptable salts of MOR receptor agonists, and polymorphs thereof, to facilitate further drug development.

SUMMARY

In a first aspect of the present disclosure, provided is a pharmaceutically acceptable salt of a compound of formula X, a polymorph of a pharmaceutically acceptable salt of the compound of formula X:

X

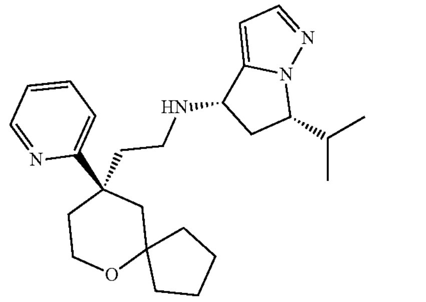

wherein the pharmaceutically acceptable salt is selected from maleate, L-tartrate, and succinate.

In some embodiments, the pharmaceutically acceptable salt of the compound of formula X and the polymorph of the pharmaceutically acceptable salt of the compound of formula X are in an anhydrous form, hydrate form, or solvent form.

In some embodiments, the polymorph is A type crystal of the maleate salt of the compound of formula X, named crystal form A, which has an X-ray powder diffraction pattern with peaks at least at the following diffraction angle 2θ (°) values: 10.06±0.2, 10.45±0.2, 11.13±0.2, 13.03±0.2, 16.81±0.2, 17.29±0.2, 19.45±0.2, 20.05±0.2, and 24.04±0.2.

In some embodiments, the polymorph is A type crystal of the maleate salt of the compound of formula X, named crystal form A, which has an X-ray powder diffraction pattern with peaks at least at the following diffraction angle 2θ (°) values: 10.06±0.2, 10.45±0.2, 11.13±0.2, 13.03±0.2, 16.81±0.2, 17.29±0.2, 19.45±0.2, 20.05±0.2, 24.04±0.2, and 37.51±0.2.

In some embodiments, the crystal form A has an X-ray powder diffraction pattern further including two or more peaks at diffraction angle 2θ (°) values selected from the group consisting of: 11.98±0.2, 14.19±0.2, 15.79±0.2, 18.52±0.2, 20.95±0.2, 21.97±0.2, and 25.57±0.2.

In some embodiments, the crystal form A has an X-ray powder diffraction pattern further including two or more peaks at diffraction angle 2θ (°) values selected from the group consisting of: 11.98±0.2, 14.19±0.2, 15.79±0.2, 18.52±0.2, 20.95±0.2, 21.97±0.2, 25.57±0.2, and 43.66±0.2.

In some embodiments, the crystal form A has an X-ray powder diffraction pattern with peaks at diffraction angle 2θ (°) values of: 10.06±0.2, 10.45±0.2, 11.13±0.2, 11.98±0.2, 13.03±0.2, 14.19±0.2, 15.79±0.2, 16.81±0.2, 17.29±0.2, 18.52±0.2, 19.45±0.2, 20.05±0.2, 20.95±0.2, 21.97±0.2, 24.04±0.2, and 25.57±0.2.

In some embodiments, the crystal form A has an X-ray powder diffraction pattern with peaks at diffraction angle 2θ (°) values of: 10.06±0.2, 10.45±0.2, 11.13±0.2, 11.98±0.2, 13.03±0.2, 14.19±0.2, 15.79±0.2, 16.81±0.2, 17.29±0.2, 18.52±0.2, 19.45±0.2, 20.05±0.2, 20.95±0.2, 21.97±0.2, 24.04±0.2, 25.57±0.2, 37.51±0.2, and 43.66±0.2.

In some embodiments, the crystal form A has an X-ray powder diffraction pattern with peaks at the 2θ (°) values shown in Table 1, and the relative intensities of the peaks are as shown in Table A1:

TABLE A1

| 2θ (°) | $I/I_0$ | 2θ (°) | $I/I_0$ | 2θ (°) | $I/I_0$ |
|---|---|---|---|---|---|
| 1.99 | W | 2.23 | W | 7.14 | W |
| 10.06 | VS | 10.45 | VS | 11.13 | S |
| 11.98 | M | 13.03 | S | 14.19 | M |
| 14.64 | W | 15.13 | W | 15.79 | M |
| 16.81 | VS | 17.29 | VS | 18.52 | M |
| 19.45 | VS | 20.05 | S | 20.95 | M |
| 21.97 | M | 24.04 | VS | 25.57 | M |
| 26.08 | W | 26.91 | W | 27.58 | W |
| 29.32 | W | 29.62 | W | 30.25 | W |
| 30.58 | W | 31.09 | W | 32.65 | W |
| 33.73 | W | 35.58 | W | 37.51 | S |
| 38.97 | W | 40.91 | W | 41.03 | W |
| 42.63 | W | 43.66 | M | 43.96 | W |

In some embodiments, the crystal form A has an X-ray powder diffraction pattern substantially as characterized in FIG. 1.

In some embodiments, the crystal form A is in an amorphous form.

In some embodiments, the crystal form A further has one or more features selected from the group consisting of:

(i) the peak temperature in the differential scanning calorimetry graph is 177.62±2° C.; in some embodiments, the differential scanning calorimetry graph is substantially as characterized in FIG. 2;

(ii) a thermogravimetric analysis graph is substantially as characterized in FIG. 3.

In some embodiments, the polymorph is the type B crystal of the L-tartrate salt of the compound of formula X, named crystal form B, which has an X-ray powder diffraction pattern with peaks at least at the following diffraction angle 2θ (°) values: 13.82±0.2, 14.87±0.2, 20.55±0.2, and 23.15±0.2.

In some embodiments, the polymorph is the type B crystal of the L-tartrate salt of the compound of formula X, named crystal form B, which has an X-ray powder diffraction pattern with peaks at least at the following diffraction angle 2θ (°) values: 13.82±0.2, 14.87±0.2, 20.55±0.2, 23.15±0.2, and 38.00±0.2.

In some embodiments, the crystal form B has an X-ray powder diffraction pattern further including two or more peaks at diffraction angle 2θ (°) values selected from the group consisting of: 10.41±0.2, 15.75±0.2, 16.28±0.2, 17.21±0.2, 17.63±0.2, 19.98±0.2, 20.22±0.2, 21.08±0.2, 22.22±0.2, 24.56±0.2, and 28.91±0.2.

In some embodiments, the crystal form B has an X-ray powder diffraction pattern further including two or more peaks at diffraction angle 2θ (°) values selected from the group consisting of: 10.41±0.2, 15.75±0.2, 16.28±0.2, 17.21±0.2, 17.63±0.2, 19.98±0.2, 20.22±0.2, 21.08±0.2, 22.22±0.2, 24.56±0.2, 28.91±0.2, and 44.21±0.2.

In some embodiments, the crystal form B has an X-ray powder diffraction pattern with peaks at diffraction angle 2θ (°) values of: 10.41±0.2, 13.82±0.2, 14.87±0.2, 15.75±0.2, 16.28±0.2, 17.21±0.2, 17.63±0.2, 19.98±0.2, 20.22±0.2, 20.55±0.2, 21.08±0.2, 22.22±0.2, 23.15±0.2, 24.56±0.2, and 28.91±0.2.

In some embodiments, the crystal form B has an X-ray powder diffraction pattern with peaks at diffraction angle 2θ (°) values of: 10.41±0.2, 13.82±0.2, 14.87±0.2, 15.75±0.2, 16.28±0.2, 17.21±0.2, 17.63±0.2, 19.98±0.2, 20.22±0.2, 20.55±0.2, 21.08±0.2, 22.22±0.2, 23.15±0.2, 24.56±0.2, 28.91±0.2, 38.00±0.2, and 44.21±0.2.

In some embodiments, the crystal form B has an X-ray powder diffraction pattern with peaks at the 2θ (°) values shown in Table B1, and the relative intensities of the peaks are as shown in Table B1:

TABLE B1

| 2θ (°) | $I/I_0$ | 2θ (°) | $I/I_0$ | 2θ (°) | $I/I_0$ |
|---|---|---|---|---|---|
| 2.12 | W | 6.50 | W | 9.56 | W |
| 9.98 | W | 10.41 | M | 11.37 | W |
| 11.82 | W | 13.82 | VS | 14.87 | VS |
| 15.75 | M | 16.28 | M | 16.82 | W |
| 17.21 | M | 17.63 | M | 18.86 | W |
| 19.31 | W | 19.98 | M | 20.22 | M |
| 20.55 | S | 21.08 | M | 21.77 | W |
| 22.22 | M | 23.15 | S | 23.71 | W |
| 24.56 | M | 27.05 | W | 28.91 | M |
| 30.11 | W | 32.45 | W | 33.26 | W |
| 35.13 | W | 38.00 | VS | 41.90 | W |
| 44.21 | M | 48.32 | W | | |

In some embodiments, the crystal form B has an X-ray powder diffraction pattern substantially as characterized in FIG. 4.

In some embodiments, the crystal form B is in an amorphous form.

In some embodiments, the crystal form B further has one or more features selected from the group consisting of:

(i) a peak temperature in a differential scanning calorimetry graph is 143.31±2° C.; in some embodiments, the differential scanning calorimetry graph is substantially as characterized in FIG. 5;

(ii) a thermogravimetric analysis graph is substantially as characterized in FIG. 6.

In some embodiments, the crystal form B has an infrared spectrum with absorption peaks at about 3457 $cm^{-1}$, 3073 $cm^{-1}$, 2959 $cm^{-1}$, 2873 $cm^{-1}$, 1716 $cm^{-1}$, 1589 $cm^{-1}$, 1571

$cm^{-1}$, 1468 $cm^{-1}$, 1440 $cm^{-1}$, 1377 $cm^{-1}$, 1287 $cm^{-1}$, 1131 $cm^{-1}$, 1105 $cm^{-1}$, 1062 $cm^{-1}$, and 799 $cm^{-1}$.

In some embodiments, the crystal form B has an infrared spectrum that is substantially as characterized in FIG. 15.

In some embodiments, the polymorph is the C-1 type crystal of the succinate salt of the compound of formula X, named crystal form C-1, which has an X-ray powder diffraction pattern with peaks at least at the following diffraction angle 2θ (°) values: 6.52±0.2, 10.37±0.2, 10.84±0.2, 13.66±0.2, 14.11±0.2, 15.61±0.2, 17.35±0.2, 20.92±0.2, and 23.20±0.2.

In some embodiments, the polymorph is the C-1 type crystal of the succinate salt of the compound of formula X, named crystal form C-1, which has an X-ray powder diffraction pattern with peaks at least at the following diffraction angle 2θ (°) values: 6.52±0.2, 10.37±0.2, 10.84±0.2, 13.66±0.2, 14.11±0.2, 15.61±0.2, 17.35±0.2, 20.92±0.2, 23.20±0.2, 37.51±0.2, and 43.61±0.2.

In some embodiments, the crystal form C-1 has an X-ray powder diffraction pattern further including peaks at diffraction angle 2θ (°) values selected from the group consisting of 19.33±0.2, and 25.09±0.2.

In some embodiments, the crystal form C-1 has an X-ray powder diffraction pattern with peaks at diffraction angle 2θ (°) values of: 6.52±0.2, 10.37±0.2, 10.84±0.2, 13.66±0.2, 14.11±0.2, 15.61±0.2, 17.35±0.2, 19.33±0.2, 20.92±0.2, 23.20±0.2, and 25.09±0.2.

In some embodiments, the crystal form C-1 has an X-ray powder diffraction pattern with peaks at diffraction angle 2θ (°) values of: 6.52±0.2, 10.37±0.2, 10.84±0.2, 13.66±0.2, 14.11±0.2, 15.61±0.2, 17.35±0.2, 19.33±0.2, 20.92±0.2, 23.20±0.2, 25.09±0.2, 37.51±0.2, and 43.61±0.2.

In some embodiments, the crystal form C-1 has an X-ray powder diffraction pattern with peaks at the 2θ (°) values shown in Table (C-1), and the relative intensities of the peaks are as shown in Table (C-1):

TABLE C-1

| 2θ(°) | $I/I_0$ | 2θ(°) | $I/I_0$ | 2θ(°) | $I/I_0$ |
|---|---|---|---|---|---|
| 1.96 | W | 5.98 | W | 6.52 | S |
| 10.37 | S | 10.84 | S | 12.34 | W |
| 12.80 | W | 13.66 | S | 14.11 | VS |
| 14.94 | W | 15.61 | S | 17.35 | S |
| 18.37 | W | 19.33 | M | 20.03 | W |
| 20.92 | S | 23.20 | VS | 24.83 | W |
| 25.09 | M | 25.88 | W | 26.77 | W |
| 28.51 | W | 29.59 | W | 31.72 | W |
| 32.80 | W | 34.58 | W | 36.20 | W |
| 37.51 | VS | 38.41 | W | 43.61 | S |

In some embodiments, the crystal form C-1 has an X-ray powder diffraction pattern substantially as characterized in FIG. 7.

In some embodiments, the polymorph is the C-2 type crystal of the succinate salt of the compound of formula X, named crystal form C-2, which has an X-ray powder diffraction pattern with peaks at least at the following diffraction angle 2θ (°) values: 37.51±0.2 and 43.64±0.2.

In some embodiments, named the crystal form C-2 has an X-ray powder diffraction pattern further including two or more peaks at diffraction angle 2θ (°) values selected from the group consisting of: 9.67±0.2, 12.55±0.2, 13.66±0.2, 14.26±0.2, 14.92±0.2, 15.70±0.2, 17.05±0.2, 17.56±0.2, 21.46±0.2, and 23.12±0.2.

In some embodiments, the crystal form C-2 has an X-ray powder diffraction pattern with peaks at diffraction angle 2θ (°) values of: 9.67±0.2, 12.55±0.2, 13.66±0.2, 14.26±0.2, 14.92±0.2, 15.70±0.2, 17.05±0.2, 17.56±0.2, 21.46±0.2, 23.12±0.2, 37.51±0.2, and 43.64±0.2.

In some embodiments, the crystal form C-2 has an X-ray powder diffraction pattern with peaks at the 2θ (°) values shown in Table (C-2), and the relative intensities of the peaks are as shown in Table (C-2):

TABLE C-2

| 2θ (°) | $I/I_0$ | 2θ (°) | $I/I_0$ | 2θ (°) | $I/I_0$ |
|---|---|---|---|---|---|
| 1.96 | W | 3.71 | W | 9.67 | M |
| 10.13 | W | 11.59 | W | 12.55 | M |
| 13.66 | M | 14.26 | M | 14.92 | M |
| 15.70 | M | 17.05 | M | 17.56 | M |
| 17.98 | W | 18.26 | W | 19.31 | W |
| 19.78 | W | 21.46 | M | 21.88 | W |
| 23.12 | M | 23.80 | W | 24.82 | W |
| 27.02 | W | 28.75 | W | 33.96 | W |
| 37.51 | VS | 43.64 | VS | | |

In some embodiments, the crystal form C-2 has an X-ray powder diffraction pattern substantially as characterized in FIG. 8.

In some embodiments, the crystal form C-2 is in an amorphous form.

In some embodiments, the crystal form C-2 further has one or more features selected from the group consisting of (i) a peak temperature in the differential scanning calorimetry graph is 117.14±2° C.; in some embodiments, the differential scanning calorimetry graph is substantially as characterized in FIG. 9;

(ii) a thermogravimetric analysis graph is substantially as characterized in FIG. 10.

In a second aspect the present disclosure, provided is a method for preparing a pharmaceutically acceptable salt of a compound of formula X including the step of:

S100: mixing the compound of formula X, an acid, and a solvent and performing a salt-forming reaction to prepare a pharmaceutically acceptable salt of the compound of formula X;

wherein, the compound of formula X has a structure of:

X

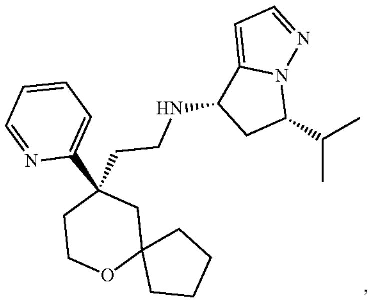

, and the acid is selected from maleic acid, L-tartaric acid, and succinic acid.

In a third aspect of the present disclosure, provided is a method for preparing a polymorph of a pharmaceutically acceptable salt of a compound of formula X, including the steps of

S210: mixing a compound of formula X, an acid and a solvent and performing a salt-forming reaction to obtain a reaction solution; and S220: subjecting the reaction solution to a crystallization treatment to obtain the polymorph;

wherein, the compound of formula X has a structure of:

X

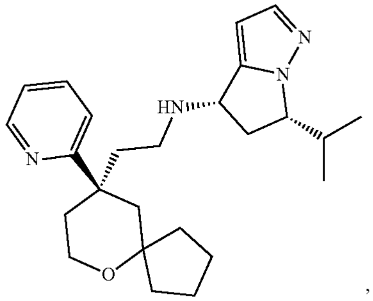

, and the acid is selected from maleic acid, L-tartaric acid, and succinic acid.

In some embodiments, in step S210, a molar ratio of the acid to the compound of formula X is about (1.1-1.3): 1, in other embodiments, 1.2:1.

In some embodiments, in Step S210, the compound of formula X, the acid, and the solvent are mixed and then reacted at a temperature of about 25° C. to about 55° C. for about 5-120 min, then at a temperature of about 25° C. to about 45° C. for about 5-120 min, and then at a temperature of about 25° C. to about 35° C. for about 5-120 min.

In some embodiments, in Step S210, the compound of formula X, the acid, and the solvent are mixed and then reacted at a temperature of about 50° C. for about 60 min, then at a temperature of about 40° C. for about 60 min, and then at a temperature of about 30° C. for about 60 min.

In some embodiments, in step S220, the crystallization treatment is performed by cooling, suspension shaking, or adding an anti-solvent.

In some embodiments, in step S220, the crystallization treatment is performed by natural cooling.

In some embodiments, the solvent in step S210 is selected from one or more of acetonitrile, water, methanol, ethanol, isopropanol, acetone, ethyl acetate, methyl tert-butyl ether, tetrahydrofuran, and n-heptane.

In some embodiments, the polymorph is crystal form A; the acid is maleic acid; and the solvent in step S210 is one or more of acetonitrile, water, methanol, ethanol, isopropanol, acetone, ethyl acetate, methyl tert-butyl ether, tetrahydrofuran, and n-heptane, in other embodiments, the solvent is ethyl acetate.

In some embodiments, the polymorph is crystal form B; the acid is L-tartaric acid; and the solvent in step S210 is one or more of acetonitrile, water, methanol, ethanol, isopropanol, acetone, ethyl acetate, methyl tert-butyl ether, tetrahydrofuran, and n-heptane, in other embodiments, the solvent is acetone.

In some embodiments, the polymorph is crystal form C-1; the acid is succinic acid; and the solvent in Step S210 is acetone.

In some embodiments, the polymorph is crystal form C-2; the acid is succinic acid; and the solvent in Step S210 is ethyl acetate.

In some embodiments, the polymorph is the polymorph described in the first aspect of the present disclosure.

In a fourth aspect of the present disclosure, provided is a method for preparing crystal form A, including the steps of S310: mixing the compound of formula X, maleic acid, and a solvent and performing a salt-forming reaction to obtain a reaction solution; and S320: subjecting the reaction solution to crystallization treatment by cooling, evaporation, suspension shaking, or adding an anti-solvent.

In some embodiments, in step S310, the solvent is selected from one or more of acetonitrile, water, methanol, ethanol, isopropanol, acetone, ethyl acetate, methyl tert-butyl ether, tetrahydrofuran, and n-heptane.

In some embodiments, in step S310, the solvent is ethyl acetate.

In some embodiments, in step S320, crystal form A is obtained by natural cooling.

In a fifth aspect of the present disclosure, provided is a method for preparing crystal form B, including the steps of S410: mixing a compound of formula X, L-tartaric acid, and a solvent and performing a salt-forming reaction to obtain a reaction solution; and S420: subjecting the reaction solution to crystallization treatment by cooling, suspension shaking, or adding an anti-solvent.

In some embodiments, in step S420, the crystallization treatment is performed by cooling or suspension shaking.

In some embodiments, in step S410, the solvent is selected from one or more of acetonitrile, water, methanol, ethanol, isopropanol, acetone, ethyl acetate, methyl tert-butyl ether, tetrahydrofuran, and n-heptane.

In some embodiments, in step S420, the product obtained after the crystallization treatment of the reaction solution is re-dissolved in a second solvent, and the crystallization treatment is performed by cooling to obtain the crystal form B. The second solvent is selected from acetonitrile, acetone, ethyl acetate, methyl tert-butyl ether, tetrahydrofuran, n-heptane, and a combination thereof.

In some embodiments, step S420 includes the following steps:

S421: cooling the reaction solution to about −10° C. to about 10° C., collecting a solid after the solid is precipitated out; and S422: dissolving the solid in a second solvent and performing crystallization by cooling to obtain crystal form B.

In some embodiments, the second solvent is acetonitrile, and step S422 includes the following steps:

S4221: dissolving the solid in acetonitrile at about 30-70° C. (in some embodiments, 60° C.) to prepare a near-saturated solution, filtering, and collecting the filtrate; and S4222: adding acetonitrile to the filtrate, cooling to about −10° C. to about 20° C. to precipitate crystals, and collecting the precipitated crystals to obtain the crystal form B.

In a sixth aspect the present disclosure, provided is a method for preparing crystal form C-1 including the steps of:

S510: mixing the compound of formula X, succinic acid, and a solvent and performing a salt-forming reaction to obtain a reaction solution; and S520: subjecting the reaction solution to crystallization treatment by cooling, evaporation, suspension shaking, or adding an anti-solvent.

In some embodiments, in step S510, the solvent is selected from acetone.

In some embodiments, in step S520, the crystallization treatment is performed by cooling.

In a seventh aspect the present disclosure, provided is a method for preparing crystal form C-2 including the steps of:

S610: mixing the compound of formula X, succinic acid, and a solvent and performing a salt-forming reaction to obtain a reaction solution; and

S620: subjecting the reaction solution to crystallization treatment by cooling, evaporation, suspension shaking, or adding an anti-solvent.

In some embodiments, in step S610, the solvent is selected from ethyl acetate.

In some embodiments, in step S620, the crystallization treatment is performed by cooling.

In an eighth aspect of the invention, provided is a pharmaceutical composition including:

(a) the pharmaceutically acceptable salt of the compound of formula X or the polymorph of the pharmaceutically acceptable salt of the compound of formula X according to the first aspect of the present disclosure, the pharmaceutically acceptable salt of the compound of formula X prepared by the method according to the second aspect, the polymorph of the pharmaceutically acceptable salt of the compound of formula X prepared by the method according to the third aspect, the crystal form A prepared by the method according to the fourth aspect, the crystal form B prepared by the method according to the fifth aspect, the crystal form C-1 prepared by the method according to the sixth aspect, or the crystal form C-2 prepared by the method according to the seventh aspect; and (b) a pharmaceutically acceptable carrier.

In a ninth aspect of the present disclosure, provided is use of the pharmaceutically acceptable salt of the compound of formula X or the polymorph of the pharmaceutically acceptable salt of the compound of formula X according to the first aspect of the present disclosure, the pharmaceutically acceptable salt of the compound of formula X prepared by the method according to the second aspect, the polymorph of the pharmaceutically acceptable salt of the compound of formula X prepared by the method according to the third aspect, the crystal form A prepared by the method according to the fourth aspect, the crystal form B prepared by the method according to the fifth aspect, the crystal form C-1 prepared by the method according to the sixth aspect, or the crystal form C-2 prepared by the method according to the seventh aspect, or the pharmaceutical composition according to the eighth aspect of the present disclosure, in the preparation of a medicament for the prevention and/or treatment of a MOR receptor agonist-mediated related disease.

In some embodiments, the MOR receptor agonist-mediated related disease is selected from pain, immune dysfunction, inflammation, esophageal reflux, neurological and psychiatric disease, urinary and reproductive disease, cardiovascular disease, and respiratory disease.

In some embodiments, the MOR receptor agonist-mediated disease is pain.

In some embodiments, the pain is selected from postoperative pain, cancer-induced pain, neuropathic pain, traumatic pain, and inflammation-induced pain.

In some embodiments, the cancer in the cancer-induced pain is selected from breast cancer, endometrial cancer, cervical cancer, skin cancer, prostate cancer, ovarian cancer, fallopian tube tumor, ovarian tumor, hemophilia, and leukemia.

In a tenth aspect of the present disclosure, provided is a method for preventing and/or treating a MOR receptor agonist-mediated related disease, including administering to a subject in need thereof a therapeutically effective amount of the pharmaceutically acceptable salt of the compound of formula X or the polymorph of the pharmaceutically acceptable salt of the compound of formula X according to the first aspect, the pharmaceutically acceptable salt of the compound of formula X prepared by the method according to the second aspect, the polymorph of the pharmaceutically acceptable salt of the compound of formula X prepared by the method according to the third aspect, the crystal form A prepared by the method according to the fourth aspect, the crystal form B prepared by the method according to the fifth aspect, the crystal form C-1 prepared by the method according to the sixth aspect, or the crystal form C-2 prepared by the method according to the seventh aspect, or the pharmaceutical composition according to the eighth aspect of the present disclosure.

It is to be understood that within the scope of the present disclosure, each of the above-mentioned features of the present disclosure and each of the features described in detail below (e.g. in the examples) may be combined with each other to form new or preferred embodiments. Limited to the text, it will not be repeated here.

The pharmaceutically acceptable salts of the compounds of formula X and the polymorph thereof of the present disclosure not only have better physicochemical stability, but also have better relevant pharmacological activities in vivo and in vitro, and thus have the potential to be further developed into drugs.

DESCRIPTION OF EMBODIMENTS

Figure 1:
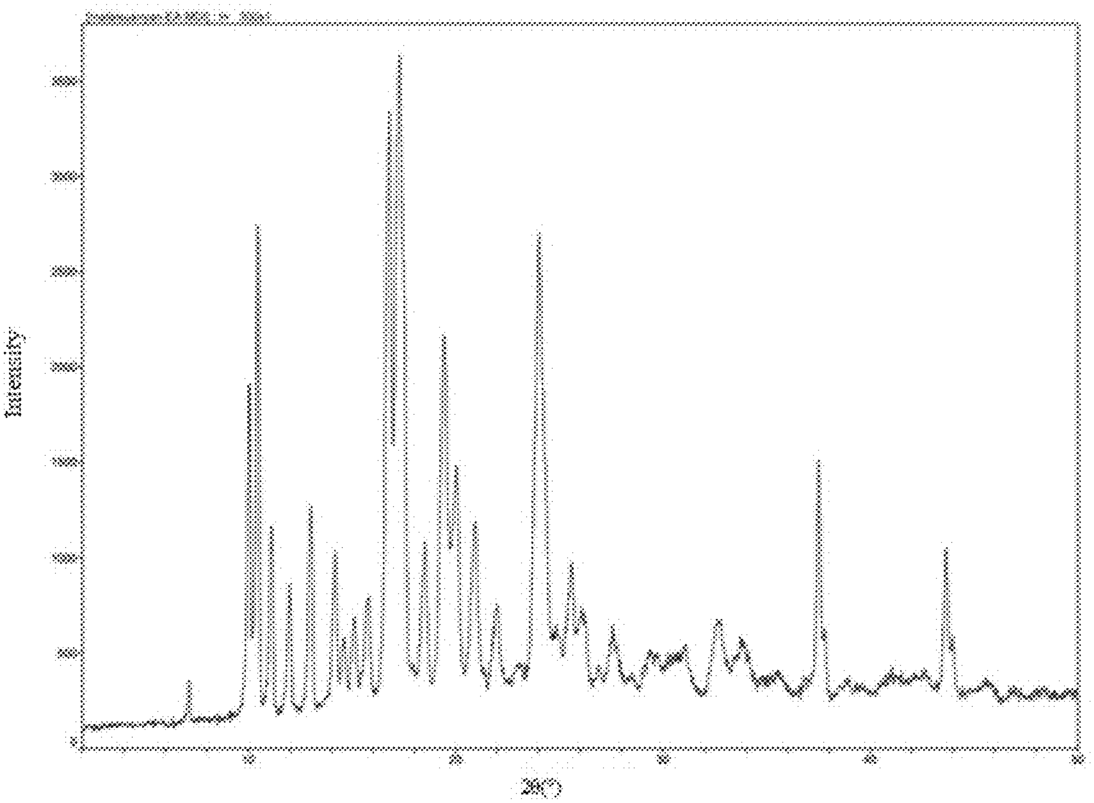
FIG. 1 shows an X-ray powder diffraction pattern of the crystal form A of Example 2 of the present disclosure.

Through extensive and in-depth studies, the inventors have found a compound of formula X having a high inhibitory activity on cAMP and a high Emax value and a low Emax value on β-arrestin, with good bias. On this basis, the pharmaceutically acceptable salts of the compound of formula X and a series of polymorphs thereof were unexpectedly found through further studies, these salts and polymorphs thereof not only have better physicochemical stability, but also have better relevant pharmacological activities in vivo and in vitro, and thus have the potential to be further developed into drugs.

Compound of Formula X

In the present disclosure, the compound of formula X is (4S,6S)-6-isopropyl-N-(2-((R)-9-(pyridin-2-yl)-6-oxaspiro[4.5]decane-9-yl)ethyl)-5,6-dihydro-4H-pyrrolo[1,2-b]pyrazol-4-amine, that has a higher inhibitory activity on cAMP and a lower Emax value on β-arrestin with an excellent bias.

The present disclosure also includes the pharmaceutically acceptable salt of the compounds of formula X and the polymorph of the pharmaceutically acceptable salt of the compound of formula X, wherein the pharmaceutically acceptable salt is selected from maleate, L-tartrate, and succinate. In this present disclosure, the polymorph includes the polymorph of the pharmaceutically acceptable salt of the compound of formula X, such as a maleate, L-tartrate, or succinate, and various solvates thereof, as well as different polymorphs of the same salt or solvate. The polymorph herein includes, but are not limited to, crystal form A, crystal form B, crystal form C-1, and crystal form C-2.

Polymorph

Solids include amorphous and crystal forms. In the case of crystal forms, the molecules are located within three-dimensional lattice sites. When a compound crystallizes from a solution or slurry, it can crystallize in a different spatial lattice arrangement (a property known as "polymorphism") to form crystals with different forms, each of which is known as a "polymorph". Different polymorphs of a given substance may differ from each other in one or more physical property, such as solubility and dissolution rate, true specific gravity, crystal form, packing pattern, flowability, and/or solid-state stability.

Crystallization

Crystallization on a production scale can be accomplished by manipulating the solution such that the solubility limit of the target compound is exceeded. This can be accomplished by a variety of methods, for example, dissolving the compound at a relatively high temperature and then cooling the solution below the saturation limit. Alternatively, the liquid volume can be reduced by boiling, atmospheric evaporation, vacuum drying, or by some other method. The solubility of the target compound can be reduced by adding an anti-solvent or a solvent in which the compound has low solubility or a mixture of such solvents. Another alternative is to adjust the pH to reduce solubility. For a detailed description of crystallization, see Crystallization, 3rd edition, J W Mullens, Butterworth-Heineman Ltd. 1993, ISBN 0750611294.

As used herein, "suspension shaking" refers to a method of mixing a compound of formula X and a corresponding acid or a solution of the corresponding acid in a suitable solvent to form a turbid solution and then shaking to obtain crystals. Suitable solvents may be water or organic solvents.

As used herein, "slowly evaporating" refers to a process wherein a solution containing a pharmaceutically acceptable salt of a compound of formula X, or a solution containing a compound of formula X and a corresponding acid, is subjected to slow evaporation to remove the solvent at a temperature to obtain crystals.

As used herein, "anti-solvent addition" or "adding an anti-solvent" refers to a method of adding another suitable solvent to a solution of a compound of formula X to obtain crystals after precipitation.

The present disclosure can be a technology in which the formation and crystallization of salt occur simultaneously, that is, if the solubility of salt in the reaction medium is lower than that of the raw material, then the addition of appropriate acid or base can lead to the direct crystallization of the desired salt. Also, in media where the final desired form is less soluble than the reactants, completion of the synthesis reaction can result in direct crystallization of the final product.

Optimization of crystallization may include seeding the crystallization medium with crystals of the desired form as seeds. In addition, many crystallization methods use a combination of the above strategies. One example is to dissolve the compound of interest in a solvent at an elevated temperature followed by addition of an appropriate volume of anti-solvent in a controlled manner so that the system is just below saturation level. At this point, seed in the desired form may be added (and the integrity of the seeds is maintained) and the system is cooled to complete crystallization.

As used herein, the term "room temperature" (RT) generally refers to about 4-30° C., in some embodiments about 20±5° C.

Identification and Properties of Polymorphs

The polymorph of the compound of formula X and the preparation process thereof can be tested and studied in various ways and apparatuses as follows.

X-ray Powder Diffraction

A polymorph of a pharmaceutically acceptable salt of a compound of formula X of the present disclosure has a specific crystal form and has specific characteristic peaks in an X-ray powder diffraction pattern (XRPD). In some embodiments, the XRPD pattern is collected on an ARL Equinox3000 X-ray powder diffraction analyzer and the XRPD parameters are as shown in the table below:

| Parameter | XRPD |
|---|---|
| X-ray source | Cu K (λ = 1.54056 Angstrom) |
| Light tube setting | 40 Kv, 30 mA |
| Detector | PSD |
| Scan range, 2θ (°) | 0°-108° |
| Scan step, 2θ (°) | 0.05 |
| Scan rate | 1 second/step |

In the X-ray powder diffractogram, the position of each peak is determined by 2θ (°). It will be appreciated that different instruments and/or conditions may result in slightly different data being generated and that the position and relative intensity of each peak may vary. Those skilled in the art should understand that when determining a crystal form according to an XRPD pattern, the peak at a low diffraction angle and the elements such as the intensity and the completeness of the peak shape are relatively more meaningful, and when the crystal form of the present disclosure is tested using the above-mentioned instrument, a strong background peak of a blank metal disk appears in the range of two positions of 2θ (°) values of high diffraction angles of 37.5-38 and 43.5-44 (the same position in FIGS. 1, 4, 7, and 8 all corresponds peaks). In the present disclosure, each crystal form has the diffraction peak with the highest peak height as the base peak, and the relative intensity thereof is defined as 100%; as $I_0$. The division of the intensities of the peaks merely reflects the approximate size of the peaks at each position. (a peak with a 2θ (°) value of 17.29 in crystal form A is a base peak; a peak with a 2θ (°) value of 13.82 in crystal form B is a base peak; a peak with a 2θ (°) value of 14.11 in crystal form C-1 is a base peak; and a peak with a 2θ (°) value of 37.51 in crystal form C-2 is a base peak). The ratio of the peak height thereof to the peak height of the base peak is taken as the relative intensity $I/I_0$ of each of the other peaks. The division of the relative intensities of each peak is defined as shown in the following table:

| Relative Intensity $I/I_0$ (%) | DEFINITION |
|---|---|
| 50-100 | VS (Very Strong) |
| 25-50 | S (Strong) |
| 10-25 | M (Medium) |
| 1-10 | W(Weak) |

Differential Scanning Calorimetry (DSC) and Thermogravimetric Analysis (TGA)

The DSC and TGA maps were collected on a DSC 25A differential scanning calorimeter and a TGA550 thermogravimetric analyzer, respectively, and the test parameters are shown in the following table:

| Parameter | DSC | TGA |
|---|---|---|
| Method | Linear temperature rise | Linear temperature rise |
| Sample pan | Aluminum pan, open | Platinum pan, covered |
| Range of temperatures | 25° C.-set temperature | 25° C.-set temperature |
| Scan Rate (° C./min) | 10 | 10 |
| Protection gas | Nitrogen | Nitrogen |

It is to be understood that additional numerical values may be obtained using other types of instruments having the same function as the instruments described above or using different test conditions than those used in the present disclosure, and accordingly, the numerical values recited are not to be taken as absolute numerical values.

Those skilled in the art can that there may be minor differences in the above parameters used to characterize the physical properties of the crystals due to instrumental errors or operator differences and the above parameters are only used to assist in characterizing the polymorphs provided by some of the examples of the present disclosure and are not to be construed as limiting the polymorphs of the present disclosure.

Infrared Spectroscopy (IR)

Agilent Cary 630 FTIR infrared spectrometer was used to test by solid KBr tablet method.

Pharmaceutical Composition of a Compound of Formula X and Use Thereof

In general, the compound of formula X, or the pharmaceutically acceptable salt thereof of the present disclosure can be administered in a suitable dosage form with one or more pharmaceutically acceptable carriers. These dosage forms are suitable for oral, rectal, topical, oral, and other parenteral administration (e.g. subcutaneous, intramuscular, intravenous, etc.). For example, dosage forms suitable for oral administration include capsules, tablets, granules, syrups, and the like. The compound of the present disclosure contained in these formulations may be solid powders or granules; solutions or suspensions in aqueous or non-aqueous liquids; water-in-oil or oil-in-water emulsions and the like. Such dosage forms can be made from the active compound and one or more carriers or adjuvants by conventional pharmaceutical procedures. Such carriers need to be compatible with the active compound or other adjuvants. For solid preparations, commonly used non-toxic carriers include but are not limited to mannitol, lactose, starch, magnesium stearate, cellulose, glucose, sucrose, and so on. Carriers for liquid preparations include water, physiological saline, aqueous dextrose, glycol, polyethylene glycol, and so on. The active compounds may form solutions or suspensions with the aforementioned carriers.

The composition of the present disclosure is formulated, dosed, and administered in a manner consistent with medical practice. The "effective amount" of the compound administered will be determined by factors such as the particular condition to be treated, the subject being treated, the cause of the condition, the target of the drug, and the mode of administration.

The present disclosure provides use of the pharmaceutically acceptable salt of the compound of formula X, or the polymorph of the pharmaceutically acceptable salt of the compound of formula X, as described in the first aspect of the present disclosure, in the preparation of a medicament for the prevention and/or treatment of a MOR receptor agonist-mediated related disease. Wherein the MOR receptor agonist-mediated related disease is selected from pain, immune dysfunction, inflammation, esophageal reflux, neurological and psychiatric disease, urinary and reproductive disease, cardiovascular disease and respiratory disease. The pain is selected from the group consisting of postoperative pain, cancer-induced pain, neuropathic pain, traumatic pain, and inflammation-induced pain. The cancer in the cancer-induced pain is selected from breast cancer, endometrial cancer, cervical cancer, skin cancer, prostate cancer, ovarian cancer, fallopian tube tumor, ovarian tumor, hemophilia, and leukemia.

As used herein, "therapeutic effective amount" refers to an amount that can produce a function or activity on humans and/or animals and can be accepted by humans and/or animals.

As used herein, "pharmaceutically acceptable carrier" refers to a non-toxic, inert, solid, semi-solid, or liquid filler, diluent, encapsulating material or auxiliary formulation or excipient of any type that is compatible with a patient, preferably a mammal, more preferably a human, and is suitable for delivering an active agent to a target site of interest without terminating the activity of the agent.

As used herein, "patient" refers to an animal, preferably a mammal, more preferably a human. The term "mammal" refers to warm-blood vertebrate mammals including, for example, cats, dogs, rabbits, bears, foxes, wolves, monkeys, deer, mice, pigs, and humans.

As used herein, "treating" refers to alleviating, delaying progression, attenuating, preventing, or maintaining an existing disease or condition (e.g. cancer). Treating also includes curing, preventing the development, or alleviating to some extent one or more of the symptoms of the disease or condition.

A therapeutically effective amount of the pharmaceutically acceptable salt of the compound of formula X, or the polymorph of the pharmaceutically acceptable salt of the compound of formula X, contained in the pharmaceutical composition of the present disclosure is from about 0.1 mg/Kg to about 5 g/kg (body weight).

EXAMPLES

The present disclosure is further illustrated below in conjunction with the following specific examples. It should be understood that the examples are only used to illustrate the present disclosure and not to limit the scope of the present disclosure. For the experimental procedures without specific conditions indicated in the following examples are generally performed according to conventional conditions or as recommended by the manufacturer. Percentages and parts are by weight unless otherwise indicated.

Reagents and Instruments

In the following examples of the present disclosure, the structure and purity of the compounds were determined by nuclear magnetic resonance ($^1$H NMR) and/or liquid mass spectrometry (LC-MS). $^1$HNMR: BrukerAVANCE-400 nuclear magnetic analyzer, with tetramethylsilane (TMS) as internal standard. LC-MS: Agilent 1290 HPLC System/6130/6150 MS LC-MS (Manufacturer: Agilent), column Waters BEH/CHS, 50×2.1 mm, 1.7 μm.

Single crystal detection was performed using a Bruker D8 venture X single crystal diffractometer. Preparative high-performance liquid chromatography (pre-HPLC): GX-281 (Manufacturer: Gilson).

ISCO Combiflash-Rf75 or Rf200 type automatic column passing instrument, and Agela 4 g, 12 g, 20 g, 40 g, 80 g, and 120 g disposable silica gel column were used.

The known starting materials in the following examples may be synthesized using or according to methods known in the art or may be purchased from companies such as ABCR GmbH & Co. KG, Acros Organics, Aldrich Chemical Company, Accela ChemBio Inc, and Darui Chemicals.

The reactions were carried out under a nitrogen or argon atmosphere unless otherwise specified in the examples. As used herein, DCE is 1,2-dichloroethane; THF is tetrahydrofuran; EA is ethyl acetate; PE is petroleum ether; DCM is dichloromethane; n-BuLi is n-butyllithium; HATU is 2-(7-azobenzotriazole)-N,N,N',N'-tetramethyluronium hexafluorophosphate; DMF is dimethylformamide; DMSO is dimethyl sulfoxide; DIEA or DIPEA is N,N-diisopropylethyl amine; DBU is 1,8-diazabicyclo[5.4.0]undec-7-ene; DIBAL-H is diisobutylaluminum hydride. Acetonitrile is ACN; methanol is MeOH; ethanol is EtOH; isopropanol is IPA; acetone is ACE; ethyl acetate is EA; methyl tert-butyl ether is MTBE; tetrahydrofuran is THF; and water is $H_2O$.

Intermediate 1a

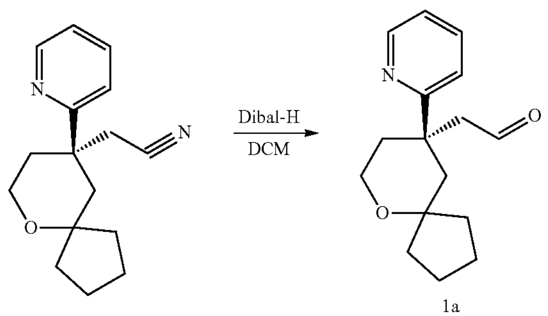 [SMILES: N#CC[C@@]1(c2ccccn2)CCOC2(CCCC2)C1 ; O=CC[C@@]1(c2ccccn2)CCOC2(CCCC2)C1]

1a (R)-2-(9-(pyridin-2-yl)-6-oxaspiro[4.5]decyl-9-yl)acetonitrile (11 g, 43 mmol, purchased from Shanghai Yucheng Pharmaceutical Technology Co. Ltd. CAS No. 1401031-38-6) was dissolved in a solution of DCM (100 ml). Diisobutylaluminum hydride solution (1.0M, 86 ml) was added dropwise at −78° C. and stirred at −78° C. for 1 hour. Sodium sulfate decahydrate (30 g) was added to the reaction solution. The mixture was stirred at room temperature for half an hour and filtered. The filtrate was concentrated under reduced pressure to give the intermediate as a yellow oil. The intermediate was dissolved in ethanol (100 ml) and a hydrochloric acid solution (6N, 100 ml) was added and stirred at 100° C. for 36 hours. The reaction solution was concentrated under reduced pressure and the obtained residue was purified by preparative liquid chromatography to give (R)-2-(9-(pyridin-2-yl)-6-oxaspiro[4.5]decyl-9-yl)acetaldehyde 1a (6.5 g), 59% yield. MS m/z (ESI): 260.2[M+1].

Intermediate 1b

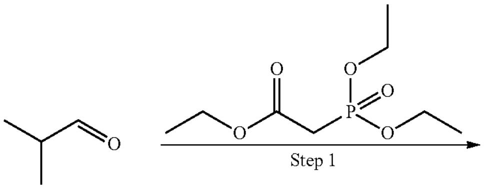

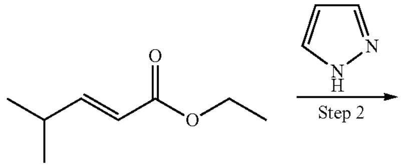

1b-1

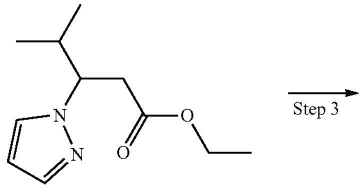

1b-2

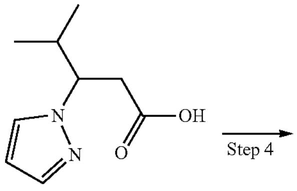

1b-3

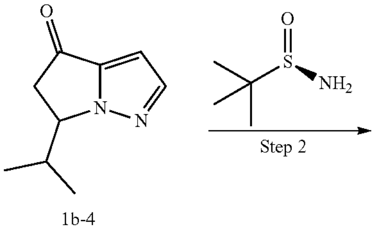

1b-4

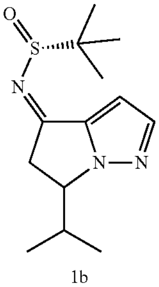

1b

Step 1: Triethyl phosphonoacetate (476 mL, 2.4 mol), DBU (365 g, 2.4 mol), lithium chloride (127 g, 3 mol), and acetonitrile (1.2 L) were added to a 3 L one-neck bottle, and stirred at room temperature under argon for 20 minutes. The reaction solution was cooled to 0° C. (internal temperature) and isobutyraldehyde (144 g, 2 mol) was slowly added dropwise. The reaction solution was stirred at room temperature for 12 hours. Upon LCMS showed the reaction was complete, After filtration, the filter cake was washed twice with EA (100 mL). Water (1 L) was added. It was extracted with EA (1.5 L) twice, washed with saturated sodium chloride, dried over anhydrous sodium sulfate, and spin-dried to give compound 1b-1 (175 g, colorless liquid).

Step 2: DMF (1 L) was added to a 3 L one-neck bottle containing compound 1b-1 (300 g, 2.1 mol), then potassium carbonate (579 g, 4.2 mol) and pyrazole (287 g, 4.2 mol) were added under stirring. The mixture was stirred at 65° C. for 18 h. Upon LC-MS showed the reaction was complete, the reaction solution was spin-dried and the remaining solid was slurried with acetonitrile (150 ml) and filtered to give a white solid. After filtration, the filter cake was washed with EA (500 mL×2). The filter cake was washed with brine (300 mL×3), dried over anhydrous sodium sulfate, spin-dried to dryness, and purified by column chromatography (PE with 5% EA as mobile phase) to give compound 1b-2 (258 g, Y: 58%, colorless liquid). MS m/z (ESI):211.1 [M+1].

Step 3: water (200 mL) was added to potassium hydroxide (133 g, 3.32 mol) to dissolve and pre-cooled (5° C.). Compound 1b-2 (465 g, 2.21 mol), methanol (0.5 L), THF (0.5 L), and a pre-cooled aqueous solution of potassium hydroxide were added to a 3 L flask, and stirred for 2 h. The reaction solution was adjusted to about pH 3 with concentrated hydrochloric acid and extracted with DCM (800 ml×2). All organic phases were combined, washed with saturated brine, dried, and concentrated to give compound 1b-3 (410.5 g, Y: 100%, white solid). MS m/z (ESI):183.1 [M+1].

Step 4: compound 1b-3 (10.2 g, 0.055 mol) and THF (200 mL) were added to a three-necked flask (500 mL) under nitrogen and cooled to −75° C. 2.5M n-butyllithium (55 mL, 0.137 mol) in THF solution was slowly added dropwise. After the addition was completed, the temperature was slowly raised to −10° C., and stirring was continued for 3 hours. The reaction was quenched with saturated ammonium chloride, added with water (100 mL), and extracted with EA (400 ml×2). The organic phases were combined, washed with saturated brine, dried, and concentrated to give a brown liquid. The brown liquid was purified by column chromatography (PE with 30% EA as mobile phase) to give compound 1b-4 (4 g, Y: 22.2%, white solid), MS m/z (ESI): 165.1 [M+1].

Step 5: compound 1b-4 (17 g, 103.5 mmol) was dissolved in 250 (mL) toluene. (R)-2-methylpropane-2-sulfinamide (18.8 g, 155 mmol) and tetraisopropyl titanate (117 g, 414 mmol) were added and stirred at 110° C. for 16 hours. After cooling to room temperature, 80 mL of water, and 600 mL of DCM were added to the reaction solution. After filtration, the filter cake was washed with DCM (100 mL). The layers were separated. The organic layer was washed with saturated brine (100 mL), dried over anhydrous sodium sulfate, and concentrated under reduced pressure. The concentrate was purified by column chromatography (PE with 30% EA as mobile phase) to give compound 1b (20.3 g, Y: 73.5%, brown liquid). MS m/z (ESI):268.1 [M+1].

Compound 1e

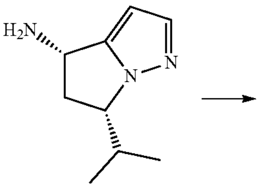

1d

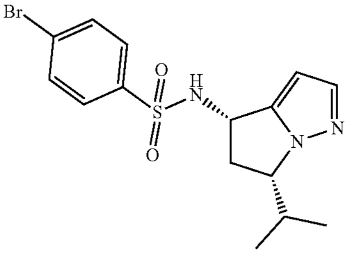

1e

Compound 1d (0.11 g, 0.67 mmol) was dissolved in dichloromethane (8 ml). Triethylamine (0.2 g, 2 mmol) and 4-bromobenzenesulfonyl chloride (0.204 g, 0.804 mmol) were added at 0° C. and stirred at 0° C. for 1 hour, then dichloromethane (10 ml) was added. The reaction solution was washed with saturated sodium chloride solution and dried over anhydrous sodium sulfate. The organic phase was concentrated under reduced pressure. The obtained residue was purified by preparative liquid chromatography to give 4-bromo-N-((4S,6S)-6-isopropyl-5,6-dihydro-4H-pyrrolo[1,2-b]pyrazol-4-yl)benzenesulfonamide 1e (0.06 g), 23.3% yield. MS m/z (ESI): 384.1[M+1].

Figure 11:
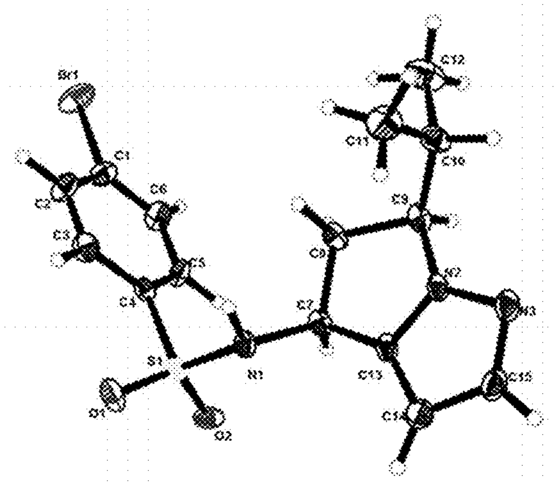
FIG. 11 shows a single crystal structure of compound 1e.

Preparation of single crystal of compound 1e: a small amount of compound 1e was placed in a small beaker and dissolved with ethyl acetate. The small beaker was sealed with a thin film, and small holes were punched in the thin film. The petroleum ether was added to a large beaker, and then the small beaker was placed into the large beaker. The large beaker was sealed. The solution was allowed to stand at room temperature for crystallization. The crystals were precipitated from the solution. Single crystal X-ray analysis of the crystal using a Bruker D8 venture X single crystal diffractometer confirmed that the absolute configuration is (4S,6S) configuration and the structure is shown in FIG. 11. Therefore, the absolute configuration of compound 1d can be inferred as (4S,6S) configuration from the single crystal structure of compound 1e.

Instrument Parameters:

| | |
|---|---|
| Light source: Mo target | Current Voltage: 50 kV, 1.4 mA |
| X-ray: Mo-Kα (λ = 0.71032 Å) | Exposure time: 3 s |
| Detector: CMOS Face Detector | Distance from face detector to sample: 50 mm |
| resolution: 0.80 Å | Test temperature: 170(2)K |

Example 1 Preparation of Compound of Formula X

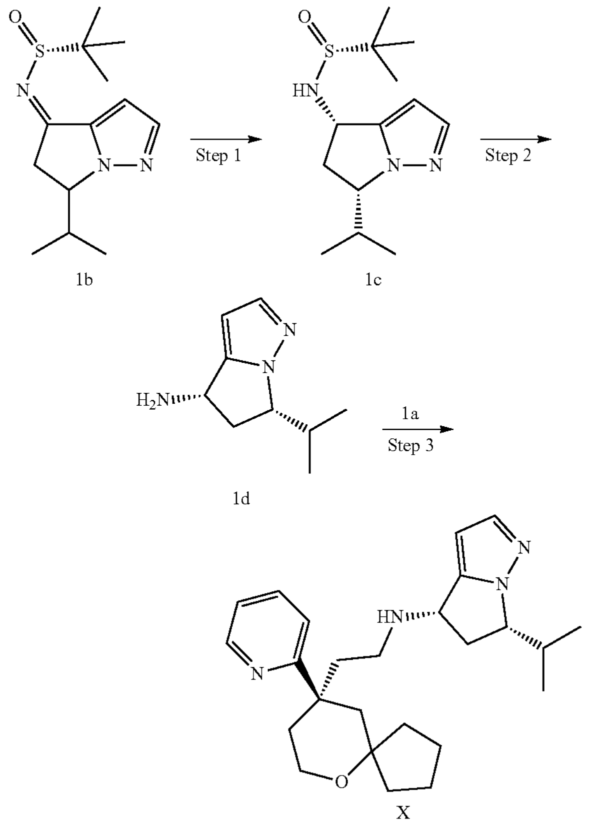

1b, 1c, 1d, X

Step 1: compound 1b (0.39 g, 1.45 mmol) and methanol (5 mL) were added into a one-neck flask. The mixture was cooled to 0° C. and added with sodium borohydride (0.11 g, 2.9 mmol) slowly. The reaction solution was stirred at room temperature for 1.5 hours. The reaction solution was cooled to 0° C., added with 20 mL of ice water, washed, and extracted with DCM (50 mL×2). The reaction solution was washed with saturated brine (20 mL), dried over anhydrous sodium sulfate, spin-dried, and purified by preparative chromatography (preparative conditions, preparative column: 21.2×250 mm C18 column, system: 10 mM $NH_4HCO_3$ $H_2O$, wavelength: 254/214 nm gradient: 28%-30% acetonitrile change) to give single diastereomer compound 1c (150 mg, yield: 38.4%, white solid, retention time: 9.5 min). MS m/z (ESI): 270.0 [M+1].

Step 2: compound 1c (120 mg, 0.45 mmol) and methanol (3 mL) were added into a one-neck flask, cooled to 0 C, and methanolic hydrogen chloride gas (1.2 mL, 4.5 mmol, 4 mol/L) was slowly added. The reaction solution was stirred at room temperature for 1.5 hours. The pH was adjusted to about 8 with saturated sodium bicarbonate. The reaction solution was extracted with DCM (50 ml×2). All organic phases were combined, washed with saturated brine, dried, and concentrated to give compound 1d (70 mg, yield: 95.12%, yellow liquid). MS m/z (ESI): 166.1[M+1].

Step 3: compound 1d (50 mg, 0.3 mmol) was dissolved in methanol (5 mL), compound 1a (78.3 mg, 0.3 mmol), and sodium cyanoborohydride (94 mg, 1.5 mmol) were added. The reaction solution was stirred at 20° C. for 3 hours. 20 mL of water was added to the reaction solution, which was extracted with DCM (30 mL×2), dried over anhydrous sodium sulfate, concentrated under reduced pressure. The concentrate was purified by preparative chromatography (preparative column: 21.2×250 mm C18 column; system: 10 mM $NH_4HCO_3$ $H_2O$; Wavelength: 254/214 nm; gradient: 30%-60% acetonitrile change) to give the compound of formula X (10.12 mg, yield: 8.26%), white solid. The absolute configuration of the compound of formula X is determined by the inference of the absolute configuration of compound 1e.

MS m/z (ESI):409.2 [M+1]; $^1H$ NMR (400 MHz, $CD_3OD$) δ 8.51 (ddd, J=4.9, 1.8, 0.8 Hz, 1H), 7.79-7.71 (m, 1H), 7.50 (d, J=8.1 Hz, 1H), 7.41 (d, J=1.9 Hz, 1H), 7.22 (ddd, J=7.5, 4.9, 1.0 Hz, 1H), 5.87 (dd, J=1.9, 0.6 Hz, 1H), 4.07 (ddd, J=21.0, 11.7, 6.2 Hz, 2H), 3.81-3.69 (m, 2H), 2.73-2.58 (m, 2H), 2.52 (dd, J=14.0, 2.3 Hz, 1H), 2.48-2.35 (m, 2H), 2.12-1.97 (m, 2H), 1.95-1.82 (m, 2H), 1.78-1.65 (m, 3H), 1.64-1.36 (m, 5H), 1.14-1.04 (m, 1H), 0.99 (d, J=7.0 Hz, 3H), 0.79-0.65 (m, 4H).

Figure 2:
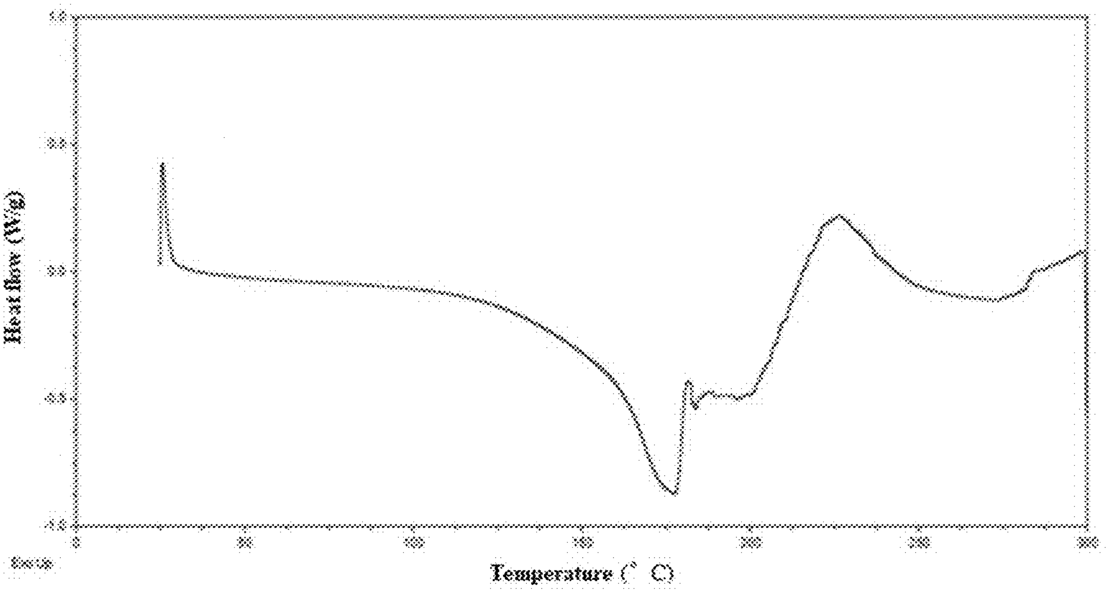
FIG. 2 shows a differential scanning calorimetry graph of the crystal form A of Example 2 of the present disclosure.
Figure 3:
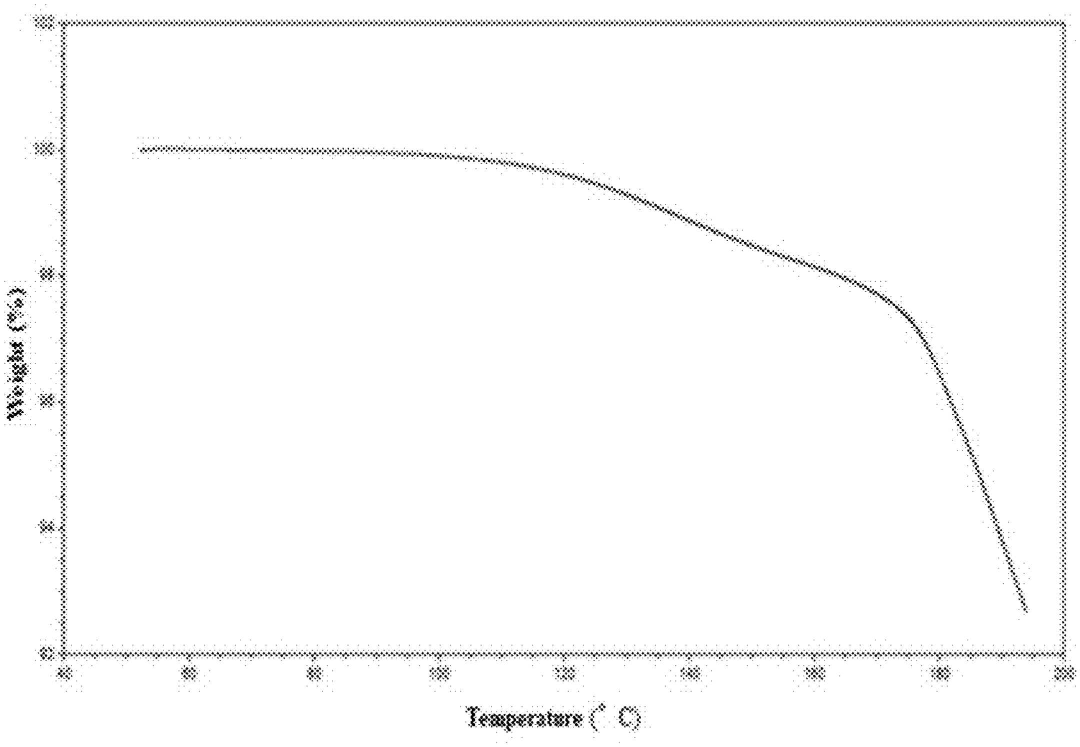
FIG. 3 shows a differential thermal analysis map of the crystal form A of Example 2 of the present disclosure.

Example 2 Preparation of Maleate Salt 500 mg of the compound of formula X was weighed by weight reduction method into a 20 ml glass sample bottle. 10 mL of ethyl acetate was added and subjected to ultra-sonic treatment to be dissolved. 1 mol/L maleic acid solution in the acid-base molar ratio of 1.2:1 was added and reacted at 50° C. for 1 h. The heating temperature was adjusted to 40° C. and stirring was continued for 1 h. The heating temperature was adjusted to 30° C. again and stirring was continued for 1 h. Finally, the heating was turned off and stirring was continued overnight. At the end of the reaction, the reaction solution was slowly cooled to 0° C. The solid precipitation was increased and centrifugation was performed to give the solid. The solvent was evaporated to dryness to give the maleate salt solid product as a crystalline powder, defined as crystal form A. The X-ray powder diffraction pattern of the obtained crystal form A is shown in FIG. 1 (2θ angle have been marked in the figure), and the differential scanning calorimetry graph and thermogravimetric analysis graph are shown in FIGS. 2 and 3, respectively, wherein the endothermic peak is 177.62° C., and the weight loss upon heating to 150° C. is 3.282%.

Figure 4:
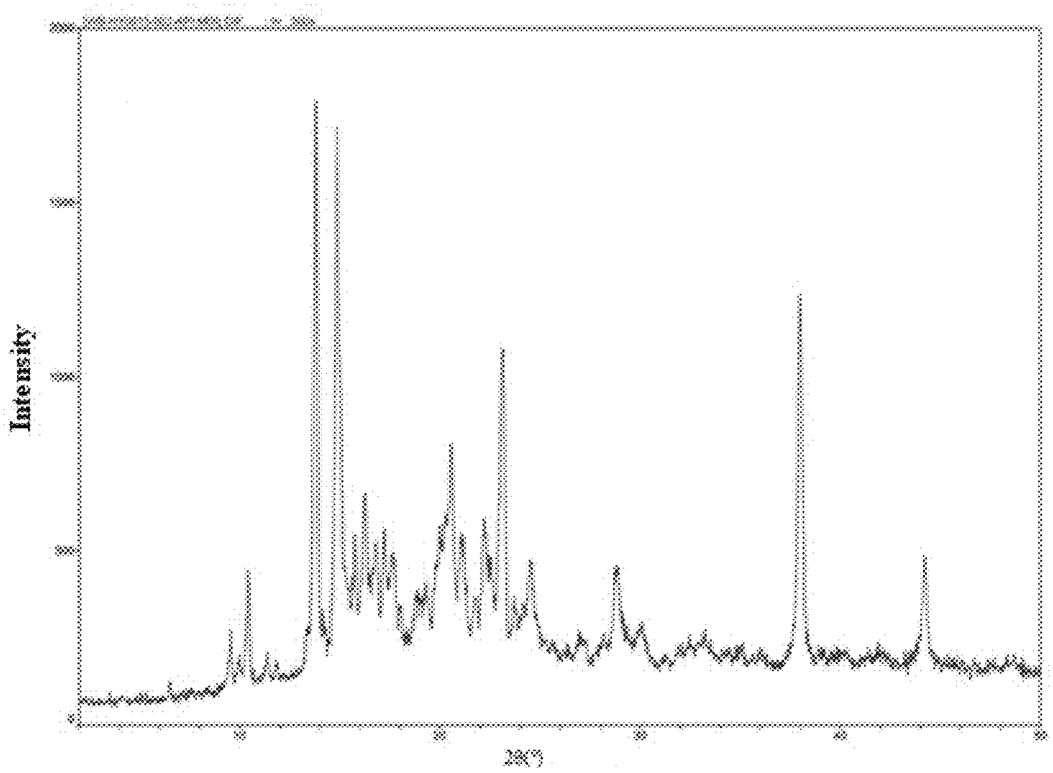
FIG. 4 shows an X-ray powder diffraction pattern of the crystal form B of Example 3a of the present disclosure.
Figure 5:
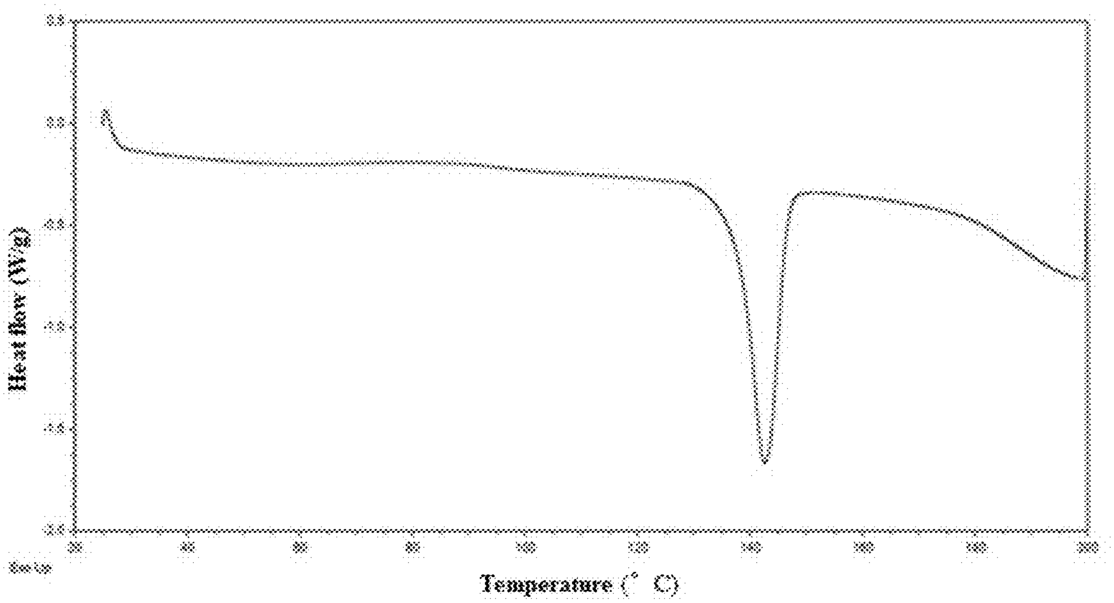
FIG. 5 shows a differential scanning calorimetry graph of the crystal form B of Example 3a of the present disclosure.
Figure 6:
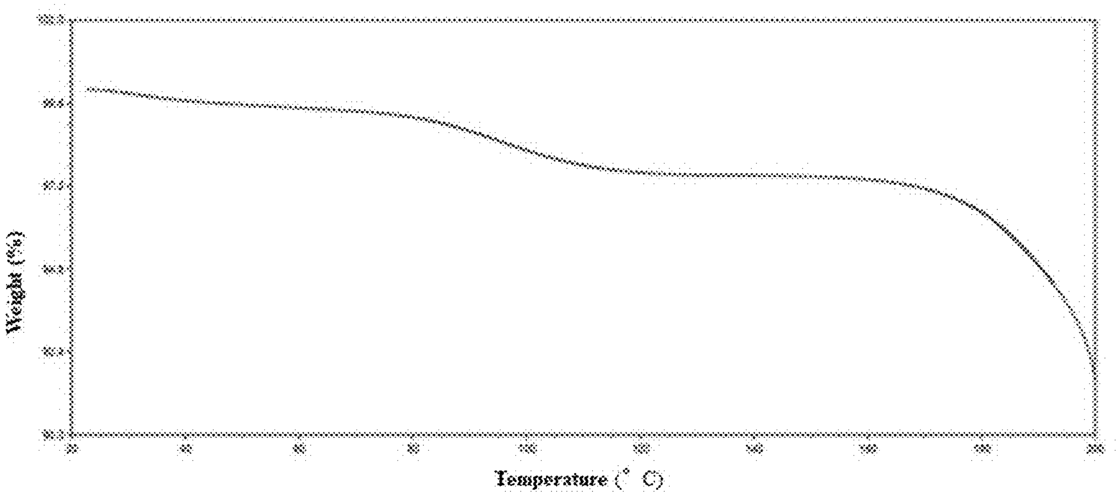
FIG. 6 shows a thermogravimetric analysis map of the crystal form B of Example 3a of the present disclosure.
Figure 15:
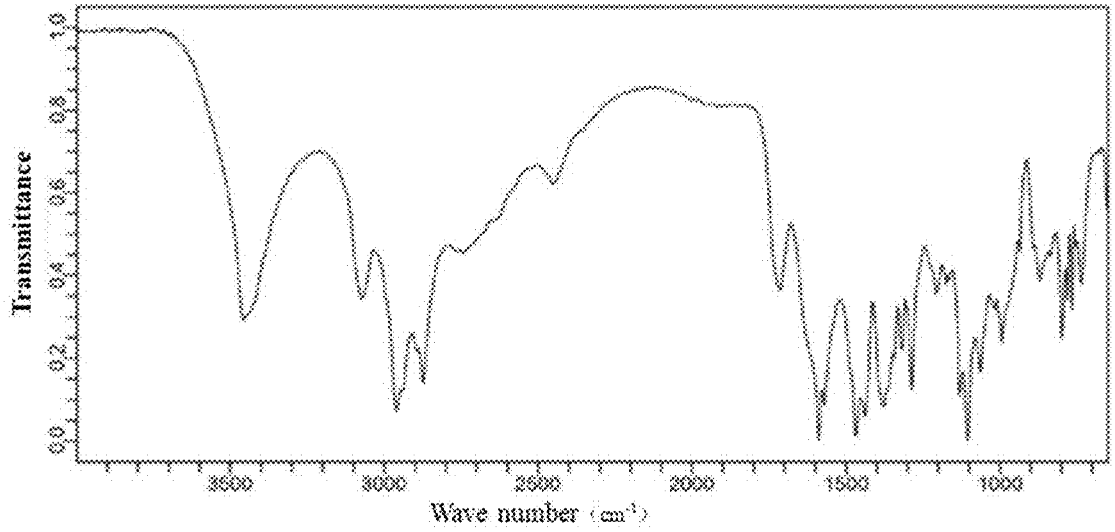
FIG. 15 is an infrared spectrum of the crystal form B.

Example 3a Preparation of L-Tartrate Salt 300 mg of the compound of formula X was weighed by weight reduction method into a 20 ml glass sample bottle. 1.5 mL of acetone was added and subjected to ultra-sonic treatment to be dissolved. 1 mol/L L-tartaric acid in the acid-base molar ratio of 1.2:1 was added for reaction at 50° C. for 1 h. The heating temperature was adjusted to 40° C. and stirring was continued for 1 h. The heating temperature was adjusted to 30° C. again and stirring was continued for 1 h. Finally, the heating was turned off and stirring was continued overnight. At the end of the reaction, the reaction solution was slowly cooled to 0° C. The solid precipitation was increased and centrifugation was performed to give the solid. The solvent was evaporated to dryness to give the L-tartrate salt of the compound of formula X as a solid product a. About 40-50 mg of the solid product a was weighed into a glass vial, added with an appropriate amount of acetonitrile at a 60° C. water bath condition, and stirred to be dissolved to give a near-saturated solution. After filtration, 20-200 μL of the corresponding solvent acetonitrile was added into the clear solution. The heating button was turned off and the temperature was slowly decreased to room temperature. The reaction solution was continued to be cooled to about 4° C. under an ice bath condition. The suspension was collected and centrifuged for 15 min under a 12000 r/min condition. The supernatant was poured. The solid was slowly evaporated at room temperature overnight and collected to give L-tartrate solid product b as a crystalline powder, defined as crystal form B. The X-ray powder diffraction pattern of the obtained crystal form B is shown in FIG. 4 (2θ angles have been marked in the figure), and the differential scanning calorimetry graph and thermogravimetric analysis graph are shown in FIGS. 5 and 6, respectively, wherein the endothermic peak is 143.31° C. and the weight loss is 0.700%. The infrared spectrum is as shown in FIG. 15.

The L-tartaric acid content of crystal form B is determined by using HPLC, found tartaric acid content: 26.0%, theoretical tartaric acid content: 26.9%. The content of tartaric acid was consistent with the theoretical value, which indicated that the salt formation ratio of the compound of formula X to L-tartaric acid was 1:1.

Example 3b Preparation of L-Tartrate Salt

Six suspension shaking experiments at 25° C. were set up with different solvent systems. About 20 mg of the solid product a obtained in example 3a was weighed into a glass vial and added with 1 mL of each organic reagent in Table 1. The vial was capped and sealed with a sealing film to prevent the liquid from volatilizing. The vial was placed at 25° C., and shaked at 25 r/min condition. The vial was taken out, and centrifuged for 15 min at 4° C., 14000 r/min condition. The supernatant was poured. The solid was slowly volatilized at room temperature overnight and the obtained solid was collected and tested by XRPD. The test results are shown in Table 1.

TABLE 1

| Solvent | Solid crystal form after shaking for 1 day | Solid crystal form after shaking for 7 days |
|---|---|---|
| Tetrahydrofuran | Form B | Form B |
| Acetonitrile | Form B | Form B |
| Ethyl acetate | Form B | Form B |
| Acetone | Form B | Form B |
| N-heptane | Form B | Form B |
| MTBE | Form B | Form B |

Example 3c Preparation of L-Tartrate Salt

Six suspension shaking experiments at 50° C. were set up with different solvent systems. About 20 mg of the solid product a obtained in example 3a was weighed into a glass vial and added with 1 mL of each organic reagent in Table 2. The vial was capped and sealed with a sealing film to prevent the liquid from volatilizing. The vial was placed at 50° C., and shaked at 225 r/min condition. The vial was taken out, and centrifuged for 15 min at 4° C., 14000/min condition. The supernatant was poured. The solid was slowly volatilized at room temperature overnight and the obtained solid was collected and tested by XRPD. The test results are shown in Table 2.

TABLE 2

| Solvent | Solid crystal form after shaking for 1 day |
|---|---|
| Acetonitrile | Form B |
| Ethyl acetate | Form B |
| Acetone | Form B |
| N-heptane | Form B |
| MTBE | Form B |

Figure 7:
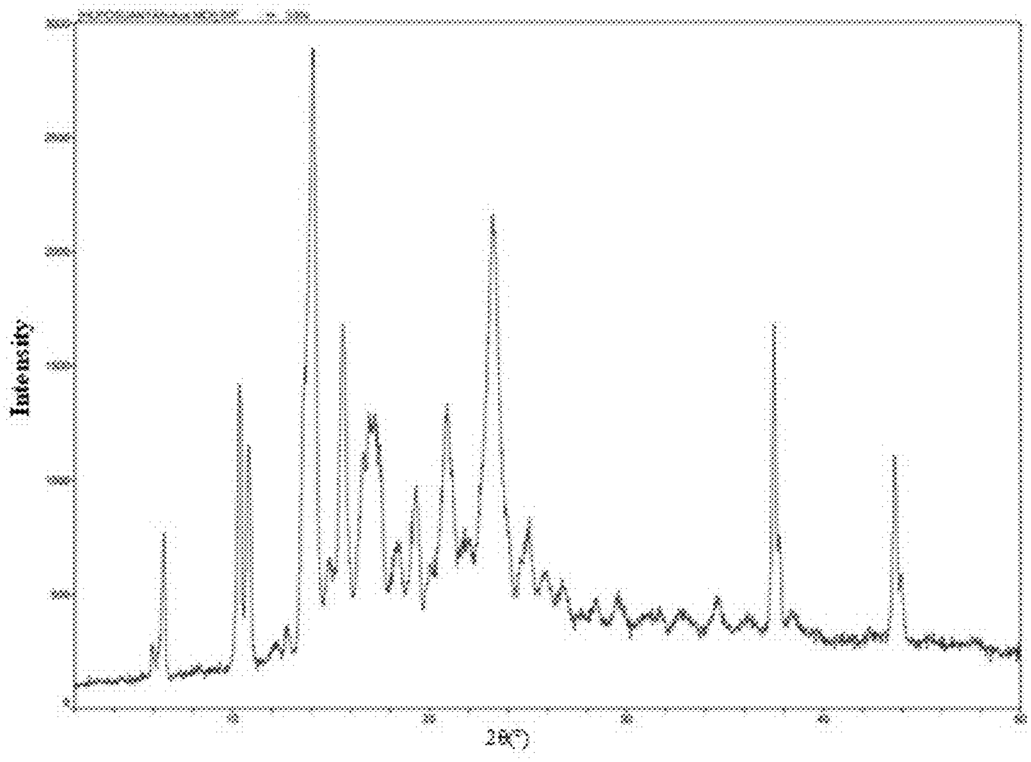
FIG. 7 shows an X-ray powder diffraction pattern of the crystal form C-1 of Example 4 of the present disclosure.

Example 4 Preparation of Succinate Salt 200 mg of the compound of formula X was weighed by weight reduction method into a 20 ml glass sample bottle. 10 mL of acetone was added and subjected to ultra-sonic treatment to be dissolved. 1 mol/L succinic acid in the acid-base molar ratio of 1.2:1 was added for reaction at 50° C. for 1 h. The heating temperature was adjusted to 40° C. and stirring was continued for 1 h. The heating temperature was adjusted to 30° C. again and stirring was continued for 1 h. Finally, the heating was turned off and stirring was continued overnight. At the end of the reaction, the reaction solution was slowly cooled to 0° C. The solid precipitation was increased and centrifugation was performed to give the solid. The solvent was evaporated to dryness to give the succinate salt solid product as a crystalline powder, defined as crystal form C-1. The X-ray powder diffraction pattern of the obtained crystal form C-1 is shown in FIG. 7 (2θ angles have been marked in the figure).

Figure 8:
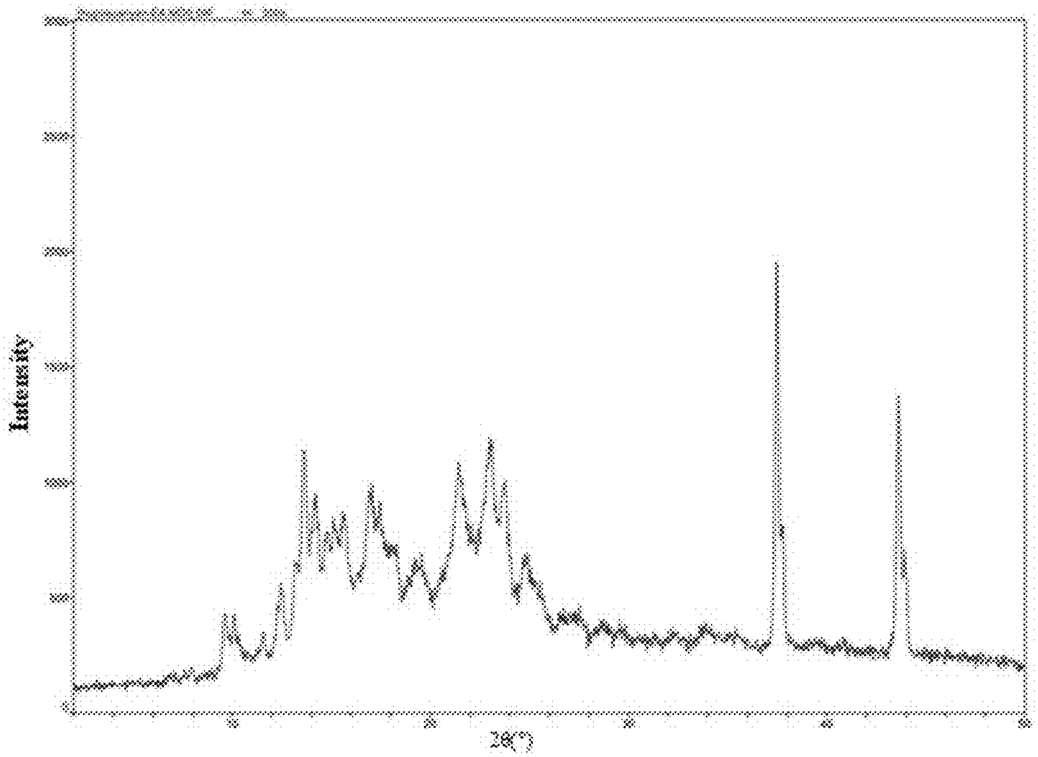
FIG. 8 shows an X-ray powder diffraction pattern of the crystal form C-2 of Example 5 of the present disclosure.
Figure 9:
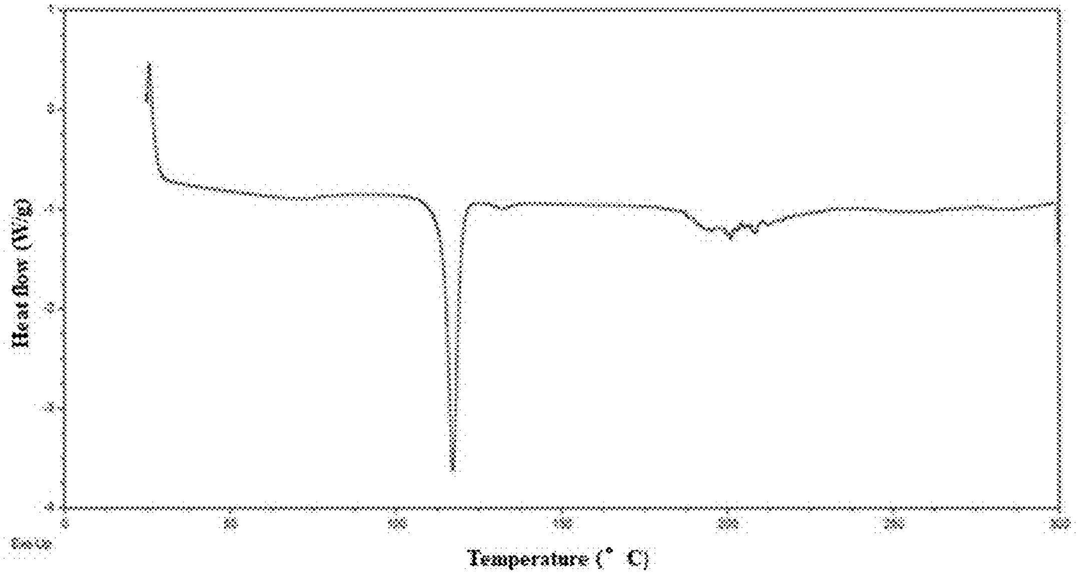
FIG. 9 shows a differential scanning calorimetry graph of the crystal form C-2 of Example 5 of the present disclosure.
Figure 10:
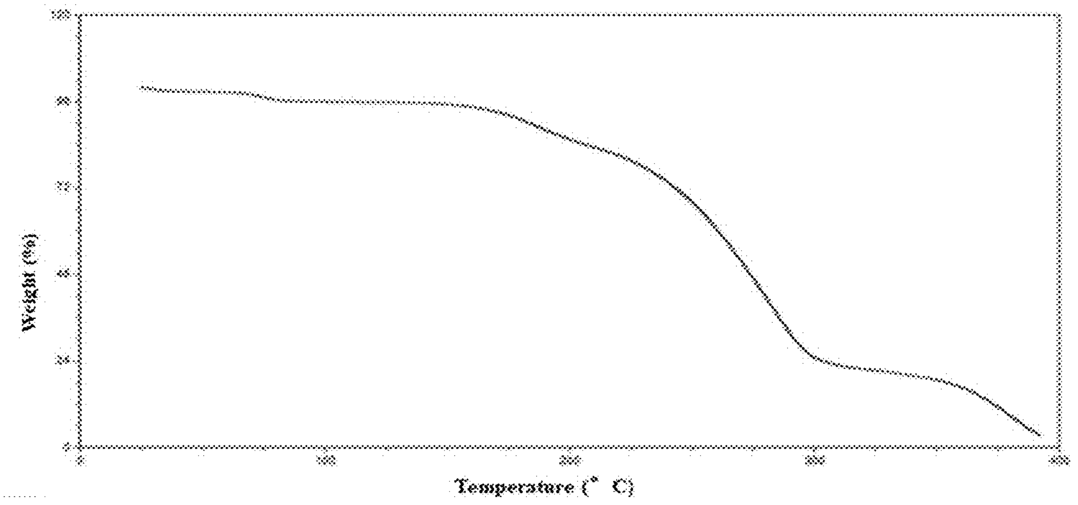
FIG. 10 shows a thermogravimetric analysis map of the crystal form C-2 of Example 5 of the present disclosure.

Example 5 Preparation of Succinate Salt 300 mg of the compound of formula X was weighed by weight reduction method into a 20 ml glass sample bottle. 1.5 mL of ethyl acetate was added and subjected to ultrasonic treatment to be dissolved. 1 mol/L succinic acid in the acid-base molar ratio of 1.2:1 was added for reaction at 50° C. for 1 h. The heating temperature was adjusted to 40° C. and stirring was continued for 1 h. The heating temperature was adjusted to 30° C. again and stirring was continued for 1 h. Finally, the heating was turned off and stirring was continued overnight. At the end of the reaction, the reaction solution was slowly cooled to 0° C. The solid precipitation was increased and centrifugation was performed to give the solid. The solvent was evaporated to dryness to give the succinate salt solid product as a crystalline powder, defined as crystal form C-2. The X-ray powder diffraction pattern of the obtained crystal form C-2 is shown in FIG. 8 (2θ angles have been marked in the figure), and the differential scanning calorimetry graph and thermogravimetric analysis graph are shown in FIGS. 9 and 10, respectively, wherein the endothermic peak is at 117.14° C. and the weight loss is 2.717% upon heating to 120° C.

Example 6 Determination of Solubility 10 mg crystal form A of maleate, crystal form B of L-tartrate, crystal form C-1 and crystal form C-2 of succinate samples were weighed and added with 1 ml of solvent respectively. The solubility tests of the samples were performed in buffer of pH4.5 (acetic acid-sodium acetate system), pH6.8 (sodium dihydrogen phosphate-sodium hydroxide system) and water at room temperature. The phenomenon was observed and the test results are shown in Table 3 (concentration in mg/ml).

TABLE 3

| | Vehicle | | | | | |
|---|---|---|---|---|---|---|
| | pH 4.5 | | pH 6.8 | | $H_2O$ | |
| Solid form | Solubility | Phenomenon | Solubility | Phenomenon | Solubility | Phenomenon |
| Crystal form C-1 | >10 | Clear | >10 | Clear | >10 | Clear |
| Crystal form C-2 | >10 | Clear | >10 | Clear | >10 | Clear |
| Crystal form A | 9.13 | Clear | 10.10 | Clear | 9.35 | Clear |
| Crystal form B | >10 | Clear | >10 | Clear | >10 | Clear |

Example 7 Stability Test

Figure 12:
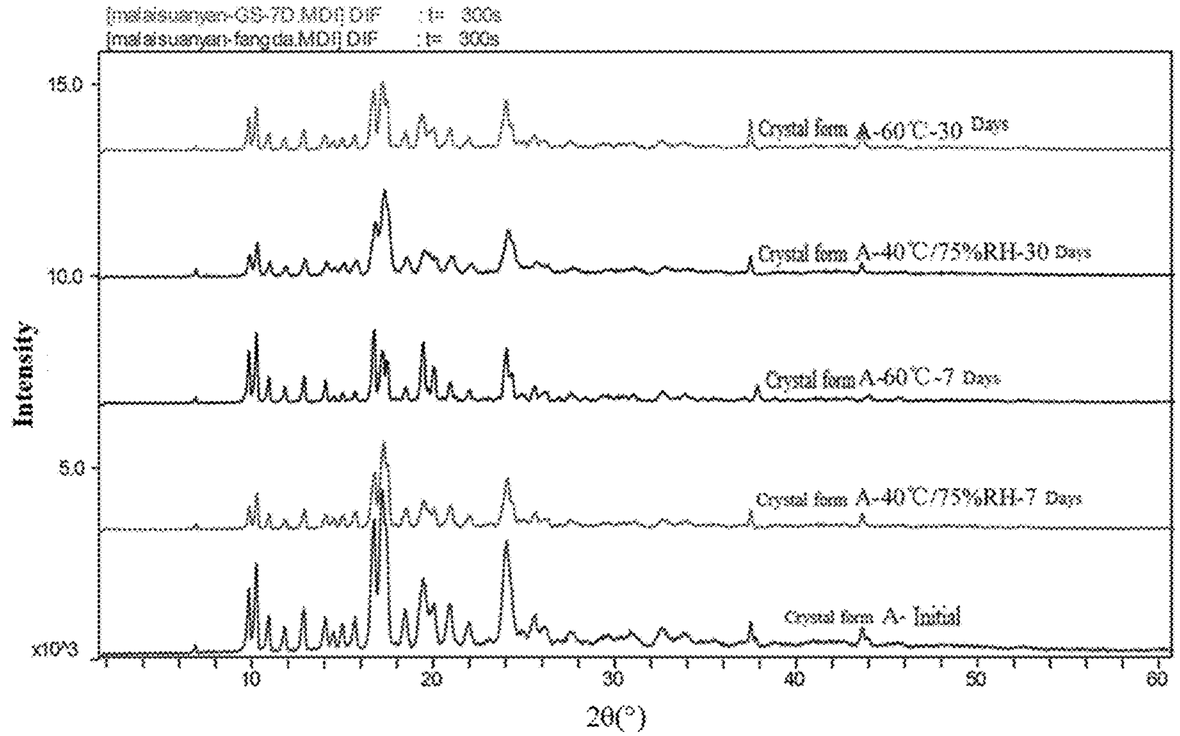
FIG. 12 shows X-ray powder diffraction patterns of the crystal form A at 60° C. and 40° C., 75% RH for 7 and 30 days.
Figure 13:
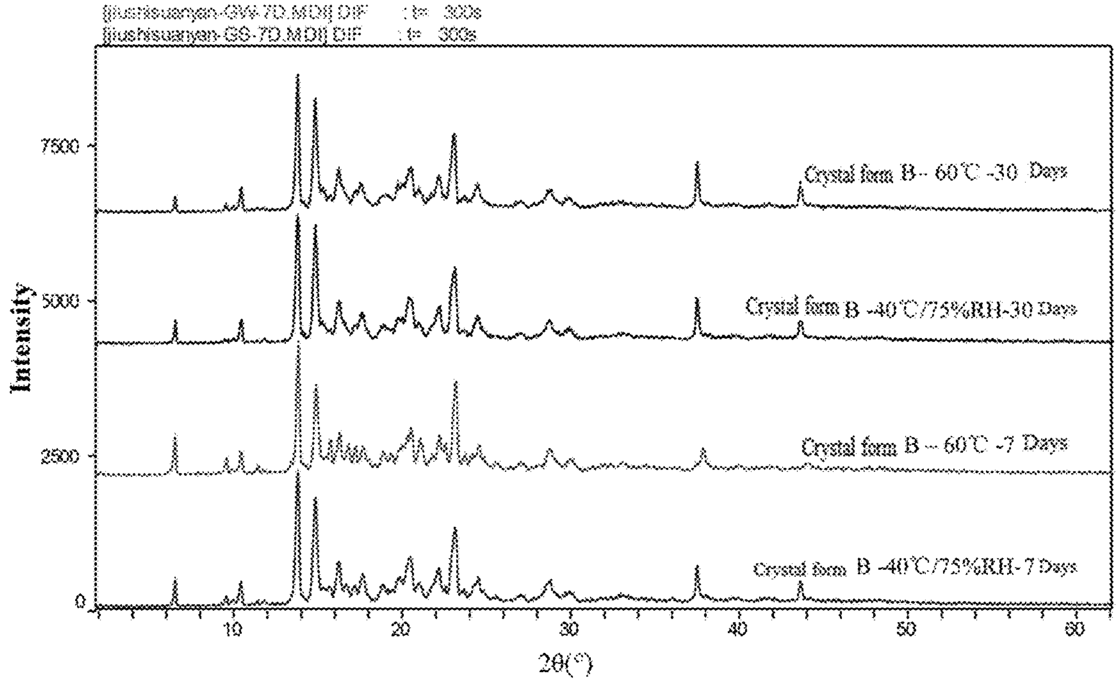
FIG. 13 shows X-ray powder diffraction patterns of the crystal form B at 60° C. and 40° C., 75% RH for 7 and 30 days.
Figure 14:
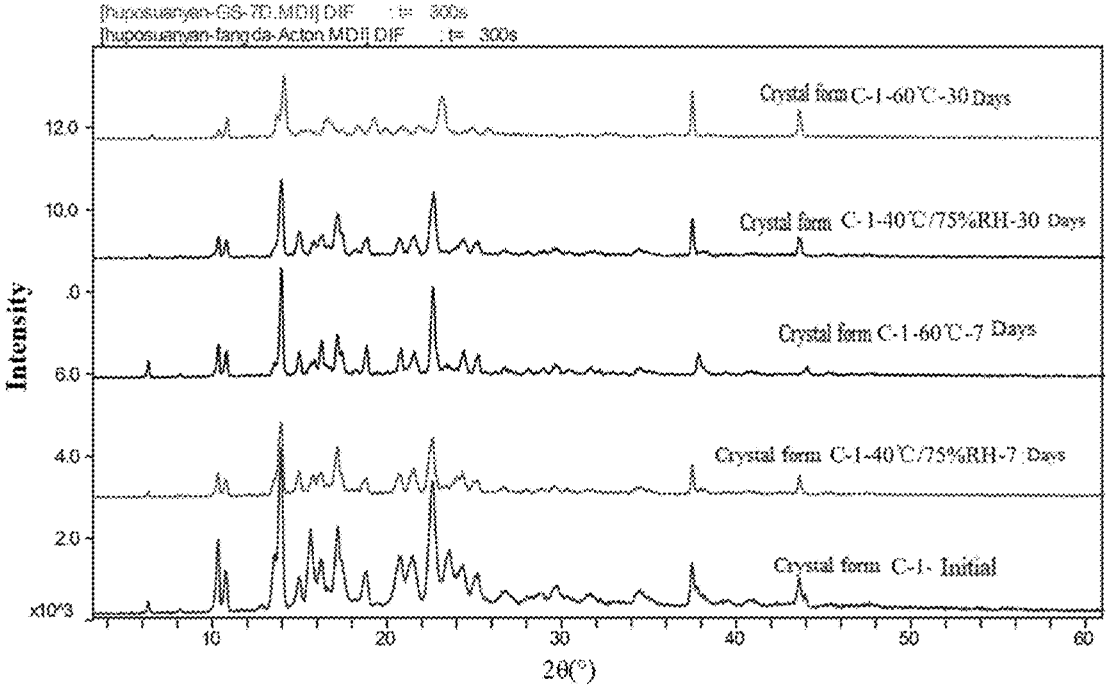
FIG. 14 shows X-ray powder diffraction patterns of the crystal form C-1 at 60° C. and 40° C., 75% RH for 7 and 30 days.

Appropriate amounts of crystal form A of maleate, crystal form B of L-tartrate and crystal form C-1 of succinate samples were weighed and placed at 60° C. and 40° C. 75% RH, respectively. While another group of samples were sealed and stored at 5° C. as the controls. The changes in crystal form and purity were detected at day 7 and day 30, respectively. As can be seen from FIGS. 12 to 14, crystal form A, crystal form B, and crystal form C-1 have good physical stability. As can be seen from Table 4, crystal form A, crystal form B, and crystal form C-1 have good chemical stability.

TABLE 4

Chemical stability data for the three crystal forms

| Sample | Relative retention time 0.668 | 0.677 | 0.717 | 0.725 | 1.025 | 1.105 |
|---|---|---|---|---|---|---|
| | Impurity content (%) | | | | | |
| Crystal form A –60° C. –7 days | 2.52 | 0.04 | 0.10 | — | 0.37 | 0.14 |
| Crystal form A –60° C. –30 days | — | 3.57 | — | 0.09 | 0.23 | 0.17 |
| Crystal form C-1 –60° C. –7 days | — | — | 0.29 | — | 0.16 | — |
| Crystal form C-1 –60° C. –30 days | — | — | — | 0.24 | 0.03 | — |
| Crystal form B –60° C. –7 days | — | — | 0.24 | — | 0.18 | — |
| Crystal form B –40° C./75% RH –30 days | — | — | — | 0.22 | — | — |
| Crystal form B –60° C. –30 days | — | — | — | 0.19 | 0.09 | 0.10 |

—indicates below the detection limit

Example 8 Hygroscopicity Test

The tests on the hygroscopicity of the samples of crystal form A of maleate, crystal form B of L-tartrate, crystal form C-1 and crystal form C-2 of succinate, were conducted according to the Guidelines for Hygroscopicity Test of Drugs (Chinese Pharmacopoeia 2020, volume IV, 9103). The results showed that under the condition of RH of 95%, crystal form C-1 and crystal form C-2 have slight hygroscopicity; crystal form A has slight hygroscopicity; and crystal form B has slight hygroscopicity.

Example 9 Bioassay

The cell line used in the following tests was PathHunter® CHO-K1 OPRM1 β-Arrestin Cell Line; origin: DiscoverX, No: 93-0213 C2; lot: 13K0402.

The reagents used, their suppliers, article numbers, and storage temperatures are as follows:

Assay Complete™ Cell Culture Kit 107, DiscoverX, 92-3107G, –20° C.;

AssayComplete™ Thawing Reagent, DiscoverX, 92-4002TR, –20° C.;

AssayComplete™ Cell Detachment Reagent, DiscoverX, 92-0009, –20° C.;

Assay Complete™ Cell Plating Reagent, DiscoverX, 93-0563R2, –20° C.;

PathhunterDetection Kit, DiscoverX, 93-0001, –20° C.;

PBS(1×)0.0067M(PO4), Hyclone, SH30256.01, 4° C.;

DMSO, Sigma, D5879-100 ML, ambient temperature;

NKH477, Sigma, 1603, –20° C.; and

IBMX, Tocris, 15879, –20° C.

The instruments used, their models and suppliers are as follows:

Countsatr BioMed, IM1200, ALIT;

Microscope, IX51, OLYMPUS;

Centrifuge, 5804, Eppendorf;

Thermostatic Water Bath, DK-S420, ShanghaiShenxian thermostatic equipment factory;

Cell Incubator, 3111, Thermo;

Biological Safety Cabinet, BSC-1300IIA2, AIRTECH;

OptiPlate-384White Opaque, 6007290, Perkin Elmer;

Multimode plate Reader, Victor X5, PerkinElmer;

Culture Plate-384 White Opaque, TC-treated, 6007680, PerkinElmer.

(1) HTRF-cAMP Cell Assay

Experimental Method and Procedures

I. Cell Resuscitation

1. The resuscitation solution was removed from the 4° C. refrigerator and placed in a 37° C. water bath for pre-heating for 15 minutes.

2. The P6 generation cells were removed from the liquid nitrogen tank and the frozen cell cryotubes were quickly placed in a 37° C. water bath with gentle shaking for 30 seconds to 1 minute until small ice crystals were seen or the cells were about to melt completely.

3. The tube was thoroughly disinfected with 70% alcohol and dried.

4. The cryopreservation solution was removed by centrifugation and the cells were resuspended with a pre-warmed fresh resuscitation solution.

a. 3 ml of pre-warmed cell resuscitation solution was pipetted into a 15 ml centrifuge tube.

b. Centrifugation was performed at 1300 rpm for 3 min.

c. The supernatant cryoprotectant was removed and the cells were resuspended with 4 ml of pre-warmed resuscitation solution.

5. The cell suspension was transferred to a T25 cell culture flask and incubated for 24 hours at 37° C., 5% $CO_2$.

6. After 24 hours of incubation, the resuscitation solution in the cell culture flask was replaced with a pre-warmed cell culture medium.

II. Cell Passage

1. When the growth density of cells in the T25 culture flask was >70%, the cells were digested and subcultured with a cell digest solution.

a. The culture medium was aspirated from the flask, and 4 ml of pre-warmed PBS was added and gently shaken to rinse the cells. The PBS was aspirated and discarded.

b. 1 ml of the cell digest solution was pipetted into a T25 flask.

c. The flask was shaken repeatedly so that the digest solution completely covered the flask, which was then placed in an incubator containing 5% $CO_2$ at 37° C. for 5 min.

d. The cell culture flask was taken out. The cells were observed under a microscope to see whether the cells were separated.

e. 3 ml of pre-warmed cell culture medium was added to stop the digestion.

f. The culture flask was repeatedly gently rinsed with the cell culture medium, and the cell suspension was collected into a 15 ml centrifuge tube.

g. Centrifugation was performed at 1300 rpm for 3 min to remove the supernatant.

h. The cells were resuspended in 3 ml of the cell culture medium.

2. The cells were passaged in a 1:3 ratio (1 ml of cell suspension+3 ml of cell culture medium were added to each flask and transferred to the T25 flask).

III. Cell Plating

1. Cell passaging steps a to h were repeated until the cells passed to the P8 generation. Cells were counted and resuspended in 2×/1 mM IBMX stimulation buffer to a cell density of 1.2*10^6/ml.

2. 1.2*10^6/ml of cell solution was seeded in a 384-well plate in a volume of 10 µl per well (i.e. 12000 cells per well) by using a multichannel pipettor.

IV. c-AMP Test

1. Relevant reagents were prepared and the compounds were prepared according to the drug dilution preparation table.

a. 1× Stimulation buffer solution: 1 ml of 5× Stimulation buffer stock solution was added into 4 ml of distilled water and mixed well.

b. 2×1 mM IBMX stimulation buffer solution 5 ml: 10 µl of 500 mM IBMX stock solution was added into a 4990 µl cell culture medium, gently pipetted, and mixed well.

c. Gradient dilution preparation table of positive drug morphine:

| Concentration of stock solution/µM | Gradient, high concentration volume (µl) | Volume of stimulation buffer (µl) | Diluted concentration/µM | Loading volume of 384-well plate (µl) | Final reaction concentration/µM |
|---|---|---|---|---|---|
| 26606 | — | — | — | — | — |
| Gradient | 1 | 19 | 1330.3 | — | — |
| 1) | 2 | 104.4 | 25 | 8 | 10.0000 |
| 2) | 20 | 40 | 8.3333 | 8 | 3.3333 |
| 3) | 20 | 40 | 2.7778 | 8 | 1.1111 |
| 4) | 20 | 40 | 0.9259 | 8 | 0.3704 |
| 5) | 20 | 40 | 0.3086 | 8 | 0.1235 |
| 6) | 20 | 40 | 0.1029 | 8 | 0.0412 |
| 7) | 20 | 40 | 0.0343 | 8 | 0.0137 |
| 8) | 20 | 40 | 0.0114 | 8 | 0.0046 |
| 9) | 20 | 40 | 0.0038 | 8 | 0.0015 |
| 10) | 20 | 40 | 0.0013 | 8 | 0.0005 |
| 11) | 20 | 40 | 0.0004 | 8 | 0.0002 |

d. Before the compounds were diluted, the compounds were solubilized with DMSO to a stock concentration of 10 mM.

Dilution preparation table for positive drug TRV130 and each compound:

| Concentration of stock solution/μM | Gradient, high concentration volume (μl) | Volume of stimulation buffer (μl) | Diluted concentration/μM | Loading volume of 384-well plate (μl) | Final reaction concentration/μM |
|---|---|---|---|---|---|
| 10000 | — | — | — | — | — |
| 1) | 1 | 399 | 25 | 8 | 10.0000 |
| 2) | 20 | 40 | 8.3333 | 8 | 3.3333 |
| 3) | 20 | 40 | 2.7778 | 8 | 1.1111 |
| 4) | 20 | 40 | 0.9259 | 8 | 0.3704 |
| 5) | 20 | 40 | 0.3086 | 8 | 0.1235 |
| 6) | 20 | 40 | 0.1029 | 8 | 0.0412 |
| 7) | 20 | 40 | 0.0343 | 8 | 0.0137 |
| 8) | 20 | 40 | 0.0114 | 8 | 0.0046 |
| 9) | 20 | 40 | 0.0038 | 8 | 0.0015 |
| 10) | 20 | 40 | 0.0013 | 8 | 0.0005 |
| 11) | 20 | 40 | 0.0004 | 8 | 0.0002 |

e. 50 μM NK477 1 ml: 1 μl of 50 mM NKH477 stock solution was added into 999 μl of 1× Stimulation buffer solution, shaken, and mixed well.

f. Detection Reagent

A. cAMP-Cryptate (donor, lyophilized) reaction solution: 1 ml of 5× cAMP-Cryptate stock solution was added into 4 ml of 1× Lysis & Detection Buffer solution and gently mixed well.

B. Anti-cAMP-d2 (acceptor, lyophilized) reaction solution: 1 ml of 5× Anti-cAMP-d2 stock solution was added into 4 ml of 1× Lysis & Detection Buffer solution and gently mixed well.

2. cAMP Test Procedure a. 12000 Cells were seeded in 10 μl of 2×IBMX stimulation buffer per well.

b. 8 μl of the compound sample dilution was added to the cells in each well.

c. 2 μl of prepared 10×NKH 477 solution was added to each well.

d. Incubation was performed for 45 mins at 37° C.

e. 10 μl of cAMP-d2 and 10 μl of anti-cAMP Cryptate reaction solution were added.

f. Incubation was performed for 60 mins at room temperature in the dark.

g. The plate was read by HTRF.

3. Reading plate was detected by RFU.

After 60 minutes of incubation, for all samples, reading plates were detected by homogeneous time-resolved fluorescence method.

Data Analysis

The data were exported from the corresponding software in the computer connected with the multi-function plate reader, including two signal values of 665 nm and 620 nm. The ratio is calculated as ratio=665 nm signal value/620 nm signal value×10000. Statistical analysis of the data was performed using Graphpad Prism software. The best-fit curve was constructed using log (agonist) vs. response. The EC50 values of the compounds were determined by computer-assisted non-linear regression analysis of dose-response curves. pEC50=−log EC50 (EC50 values are expressed in moles); maximum effect value of % Morphine=(compound sample ratio−blank well ratio)/TOP×100 (Note: the TOP value is the curve Top value fitted by software Graphpad Prism analysis after the morphine sample ratio−blank well ratio). The results are shown in Table 5:

TABLE 5

Activities of compounds on cAMP

| Compound | cAMP $EC_{50}$ (nM) | cAMP Emax(%) Morphine, 100% |
|---|---|---|
| Compound of formula X | 6.0 | 86.4 |
| Comparative compound D1 | 19 | 52.6 |

The structure of the comparative compound D1 is shown below, which can be prepared by referring to the method described in CN111662284A.

D1

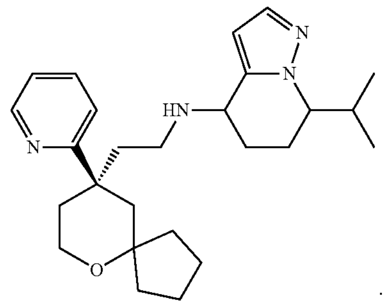

(2) β-Arrestin Cell Assay

Experimental Method and Procedures

I. Cell Resuscitation

1. The resuscitation solution was removed from the 4° C. refrigerator and placed in a 37° C. water bath for pre-heating for 15 minutes.

2. The P6 generation cells were removed from the liquid nitrogen tank and the frozen cell culture tubes were quickly placed in a 37° C. water bath with gentle shaking for 30 seconds to 1 minute until small ice crystals were seen or the cells were about to melt completely.

3. The tube was thoroughly disinfected with 70% alcohol and dried.

4. The cryopreservation solution was removed by centrifugation and the cells were resuspended with a pre-warmed fresh resuscitation solution.

a. 3 ml of pre-warmed cell resuscitation solution was pipetted into a 15 ml centrifuge tube.

b. Centrifugation was performed at 1300 rpm for 3 min.

c. The supernatant was removed and the cells were resuspended with 4 ml of pre-warmed resuscitation solution.

5. The cell suspension was transferred to a T25 cell culture flask and incubated for 24 hours at 37° C., 5% $CO_2$.

6. After 24 hours of incubation, the resuscitation solution in the cell culture flask was replaced with a pre-warmed cell culture medium.

II. Cell Passage

1. When the growth density of cells in the T25 culture flask was >70%, the cells were digested and subcultured with a cell digest solution.

a. The culture medium was aspirated from the flask, 4 ml of pre-warmed PBS was added and gently shaken to rinse the cells. The PBS was aspirated and discarded.

b. 1 ml of the cell digest solution was pipetted into a T25 flask.

c. The flask was shaken repeatedly so that the digest solution completely covered the flask, which was then placed in an incubator containing 5% $CO_2$ at 37° C. for 5 min.

d. The cell culture flask was taken out. The cells were observed under a microscope to see whether the cells were separated.

e. 3 ml of pre-warmed cell culture medium was added to stop digestion.

f. The culture flask was repeatedly gently rinsed with the cell culture medium and finally the cell suspension was transferred to a 15 ml centrifuge tube.

g. Centrifugation was performed at 1300 rpm for 3 min to remove the supernatant.

h. The cells were resuspended in 3 ml of the cell culture medium.

2. The cells were passaged in a 1:3 ratio (1 ml of cell suspension+3 ml of cell culture medium were added to each flask and transferred to the T25 flask).

3. Cell passaging steps a to h were repeated until the cells passed to the P8 generation.

III. Cell Plating 1. 20 μl of the cell suspension was pipetted using a pipette and the number of the cells was measured using a cell counter.

2. The centrifugation was performed at 1300 rpm for 3 minutes to precipitate the cells.

3. The supernatant was removed and the corresponding cell plating solution was added to make the cell concentration of $2\times10^5$/ml.

4. $2\times10^5$/ml cell solution was seeded in a 384 well plate in a volume of 20 μl per well (i.e. 4000 cells per well) using a multichannel pipette according to the experimental design.

5. The 384-well plate with well-seeded cells was placed into a 37° C., 5% $CO_2$ incubator for incubating for 24 h.

IV. β-Arrestin Test

1. The compounds were formulated according to the following dilution table.

a. Gradient dilution preparation table of positive drug morphine:

| Concentration of stock solution/ μM | Gradient, high concentration volume (μl) | Volume of added Plating Buffer (μl) | Volume of added DMSO (μl) | Diluted concentration/ μM | Loading volume of 384-well plate (μl) | Final reaction concentration/ μM |
|---|---|---|---|---|---|---|
| 26606 | — | — | — | — | — | — |
| Prepare | 2 | 18 | 0 | 2660.6 | — | — |
| A | 2 | 101.763 | 2.661 | 50.000 | 5 | 10.000 |
| B | 20 | 39 | 1 | 16.667 | 5 | 3.333 |
| C | 20 | 39 | 1 | 5.556 | 5 | 1.111 |
| D | 20 | 39 | 1 | 1.852 | 5 | 0.370 |
| E | 20 | 39 | 1 | 0.617 | 5 | 0.123 |
| F | 20 | 39 | 1 | 0.206 | 5 | 0.041 |
| G | 20 | 39 | 1 | 0.069 | 5 | 0.014 |
| H | 20 | 39 | 1 | 0.023 | 5 | 0.005 |

b. Before the compounds were diluted, the compounds were solubilized with DMSO to a stock concentration of 10 mM.

Dilution preparation table for positive drug TRV130 and each compound:

| Concentration of stock solution/ μM | Gradient, high concentration volume (μl) | Volume of added DMSO (μl) | Diluted concentration/ μM | Volume of diluted solution (μl) | Volume of added Plating Buffer (μl) | Final diluted concentration/ μM | Loading volume of 384-well plate (μl) | Final reaction concentration/ μM |
|---|---|---|---|---|---|---|---|---|
| 10000 | — | — | — | — | — | — | — | — |
| A | 12.5 | 50 | 2000 | 2.5 | 97.5 | 50.000 | 5 | 10.000 |
| B | 20 | 40 | 666.667 | 2.5 | 97.5 | 16.667 | 5 | 3.333 |
| C | 20 | 40 | 222.222 | 2.5 | 97.5 | 5.556 | 5 | 1.111 |
| D | 20 | 40 | 74.074 | 2.5 | 97.5 | 1.852 | 5 | 0.370 |
| E | 20 | 40 | 24.691 | 2.5 | 97.5 | 0.617 | 5 | 0.123 |
| F | 20 | 40 | 8.230 | 2.5 | 97.5 | 0.206 | 5 | 0.041 |
| G | 20 | 40 | 2.743 | 2.5 | 97.5 | 0.069 | 5 | 0.014 |
| H | 20 | 40 | 0.914 | 2.5 | 97.5 | 0.023 | 5 | 0.005 |

2. 5 μl of each compound sample dilution prepared above was added to a 384 well plate.

3. After adding the sample, the 384-well plate was put back to the 37° C., 5% $CO_2$ incubator for incubating for 90 minutes.

V. Relative Light Unit Value (RLU) Detection

1. Working Detection solutions in the following proportions were prepared (pay attention to avoid light) before the end of compound incubation. Then, 12.5 μl was added to each well, and incubated for 1 h at room temperature in a shaker in the dark.

| Components | Proportion |
|---|---|
| Cell Assay Buffer | 19 |
| Substrate Reagent 1 | 5 |
| Substrate Reagent 2 | 1 |
| Total volume | 25 |

2. At the end of compound incubation, 12.5 μl of the above working solution was added to each well, and incubated for 1 h at room temperature in an shaker at 80 rpm in the dark.

3. At the end of incubation, the plates were read using a multi-function plate reader.

Data Analysis

The data were exported from the corresponding software in the computer connected with the multi-function plate reader, and the data were analyzed by using GraphPad Prism software. The best-fit curve was constructed using log (agonist) vs. response. The EC50 values of the compounds were determined by computer-assisted non-linear regression analysis of dose-response curves. pEC50=−log EC50 (EC50 values are expressed in moles); maximum effect value of % morphine=(RLU value of compound sample−RLU value of blank well)/TOP×100 (Note: the TOP value is the curve Top value fitted by software Graphpad Prism analysis after the RLU value of the morphine sample−the RLU value of the blank well). The results are shown in Table 6:

TABLE 6

Test results of compounds on β-arrestin

| Compound | β-arrestin Emax(%) Morphine, 100% |
|---|---|
| Compound of formula X | 1.3 |
| Comparative compound D1 | 28.3 |

As can be seen from Tables 5 and 6, the compound of formula X has a higher inhibitory activity on cAMP and a higher Emax value than the comparative compound D1. Furthermore, the compound of formula X has a lower Emax value for β-arrestin and a better bias.

All references mentioned in this application are incorporated herein by reference as if each reference were individually incorporated by reference. Furthermore, it will be appreciated that those skilled in the art, upon reading the teachings of the present application, may make various changes and modifications to the present application and that such equivalents are intended to fall within the scope of the appended claims of the present application.

What is claimed is:

1. A pharmaceutically acceptable salt of a compound of formula X, the compound of formula X having a structure of:

X

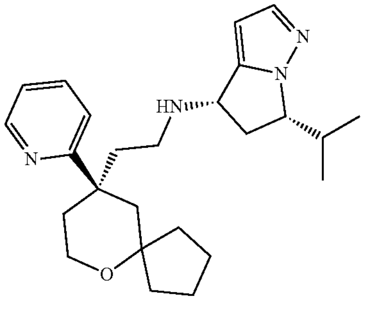

wherein the pharmaceutically acceptable salt is a maleate, L-tartrate, or succinate; and wherein the pharmaceutically acceptable salt of the compound of formula X is a polymorph selected from any one of the following crystal forms:

A type crystal of the maleate salt of the compound of formula X, named crystal form A, which has an X-ray powder diffraction pattern with peaks at least at the following diffraction angle 2θ(°) values: 10.06±0.2, 10.45±0.2, 11.13±0.2, 13.03±0.2, 16.81±0.2, 17.29±0.2, 19.45±0.2, 20.05±0.2, and 24.04±0.2;

B type crystal of the L-tartrate salt of the compound of formula X, named crystal form B, which has an X-ray powder diffraction pattern with peaks at least at the following diffraction angle 2θ(°) values: 13.82±0.2, 14.87±0.2, 20.55±0.2, and 23.15±0.2;

C-1 type crystal of the succinate salt of the compound of formula X, named crystal form C-1, which has an X-ray powder diffraction pattern with peaks at least at the following diffraction angle 2θ(°) values: 6.52±0.2, 10.37±0.2, 10.84±0.2, 13.66±0.2, 14.11±0.2, 15.61±0.2, 17.35±0.2, 20.92±0.2, and 23.20±0.2; and C-2 type crystal of the succinate salt of the compound of formula X, named crystal form C-2, which has an X-ray powder diffraction pattern with peaks at least at the following diffraction angle 2θ(°) values: 9.67±0.2, 12.55±0.2, 13.66±0.2, 14.26±0.2, 14.92±0.2, 15.70±0.2, 17.05±0.2, 17.56±0.2, 21.46±0.2, 23.12±0.2, 37.51±0.2, and 43.64±0.2.

2. The pharmaceutically acceptable salt of the compound of formula X according to claim 1, wherein:

the crystal form A has an X-ray powder diffraction pattern substantially as characterized in FIG. 1;

the crystal form B has an X-ray powder diffraction pattern substantially as characterized in FIG. 4;

the crystal form C-1 has an X-ray powder diffraction pattern substantially as characterized in FIG. 7; and the crystal form C-2 has an X-ray powder diffraction pattern substantially as characterized in FIG. 8.

3. The pharmaceutically acceptable salt of the compound of formula X according to claim 1, wherein the X-ray powder diffraction pattern of the crystal form B further comprises two or more peaks at diffraction angle 2θ(°) values selected from the group consisting of: 10.41±0.2, 15.75±0.2, 16.28±0.2, 17.21±0.2, 17.63±0.2, 19.98±0.2, 20.22±0.2, 21.08±0.2, 22.22±0.2, 24.56±0.2, and 28.91±0.2.

4. The pharmaceutically acceptable salt of the compound of formula X according to claim 1, wherein the crystal form B further has one or more features selected from the group consisting of:

(i) a peak temperature in a differential scanning calorimetry graph is 143.31±2° C.; the differential scanning calorimetry graph is substantially as characterized in FIG. 5;

(ii) a thermogravimetric analysis graph is substantially as characterized in FIG. 6; and (iii) an infrared spectrum is substantially as characterized in FIG. 15.

5. A method for preparing a polymorph of a pharmaceutically acceptable salt of a compound of formula X, comprising the steps of:

(i) mixing the compound of formula X, an acid and a solvent and performing a salt-forming reaction to obtain a reaction solution;

(ii) subjecting the reaction solution to a crystallization treatment to obtain the polymorph;

wherein, the compound of formula X has a structure of:

X

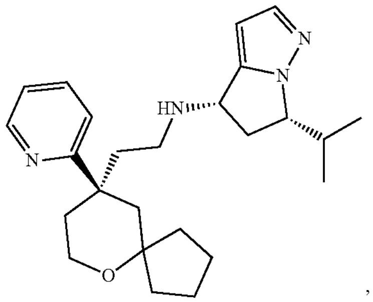

, and the acid is selected from maleic acid, L-tartaric acid, and succinic acid; and wherein the polymorph is selected from any one of the following crystal forms:

A type crystal of the maleate salt of the compound of formula X, named crystal form A, which has an X-ray powder diffraction pattern with peaks at least at the following diffraction angle 2θ(°) values: 10.06±0.2, 10.45±0.2, 11.13±0.2, 13.03±0.2, 16.81±0.2, 17.29±0.2, 19.45±0.2, 20.05±0.2, and 24.04±0.2;

B type crystal of the L-tartrate salt of the compound of formula X, named crystal form B, which has an X-ray powder diffraction pattern with peaks at least at the following diffraction angle 2θ(°) values: 13.82±0.2, 14.87±0.2, 20.55±0.2, and 23.15±0.2;

C-1 type crystal of the succinate salt of the compound of formula X, named crystal form C-1, which has an X-ray powder diffraction pattern with peaks at least at the following diffraction angle 2θ(°) values: 6.52±0.2, 10.37±0.2, 10.84±0.2, 13.66±0.2, 14.11±0.2, 15.61±0.2, 17.35±0.2, 20.92±0.2, and 23.20±0.2; and C-2 type crystal of the succinate salt of the compound of formula X, named crystal form C-2, which has an X-ray powder diffraction pattern with peaks at least at the following diffraction angle 2θ(°) values: 9.67±0.2, 12.55±0.2, 13.66±0.2, 14.26±0.2, 14.92±0.2, 15.70±0.2, 17.05±0.2, 17.56±0.2, 21.46±0.2, 23.12±0.2, 37.51±0.2, and 43.64±0.2.

6. The preparation method according to claim 5, wherein the step of mixing the compound of formula X, an acid and a solvent and performing a salt-forming reaction comprises the step of:

mixing and reacting the compound of formula X, the acid and the solvent at a temperature of 25° C.-55° C. for 5-120 min, then reacting at a temperature of 25° C.-45° C. for 5-120 min, and then reacting at a temperature of 25° C.-35° C. for 5-120 min.

7. The preparation method according to claim 5, wherein the crystallization treatment is performed by cooling, suspension shaking, or adding an anti-solvent; or the crystallization treatment is performed by natural cooling.

8. The preparation method according to claim 5, wherein the polymorph is the crystal form A; the acid is maleic acid; and the solvent is acetonitrile, water, methanol, ethanol, isopropanol, acetone, ethyl acetate, methyl tert-butyl ether, tetrahydrofuran, n-heptane, or a combination thereof; or the polymorph is the crystal form B; the acid is L-tartaric acid; and the solvent is acetonitrile, water, methanol, ethanol, isopropanol, acetone, ethyl acetate, methyl tert-butyl ether, tetrahydrofuran, n-heptane, or a combination thereof; or the polymorph is the crystal form C-1; the acid is succinic acid; and the solvent is acetone; or the polymorph is the crystal form C-2; the acid is succinic acid; and the solvent is ethyl acetate.

9. The preparation method according to claim 5, wherein the polymorph is the crystal form B, and the crystallization treatment comprises the steps of:

cooling the reaction solution to −10° C. to 10° C., and collecting a solid; and dissolving the solid in a second solvent and performing crystallization by cooling to obtain the crystal form B, the second solvent being selected from tetrahydrofuran, acetonitrile, ethyl acetate, acetone, n-heptane, and methyl tert-butyl ether.

10. The preparation method according to claim 9, wherein the second solvent is acetonitrile, and the step of dissolving the solid in the second solvent and performing crystallization by cooling to obtain the crystal form B comprises the steps of:

dissolving the solid in acetonitrile at 30-70° C. to prepare a near saturated solution, filtering, and collecting the filtrate; and adding acetonitrile to the filtrate, cooling to −10° C. to 20° C., and collecting the precipitated crystals to obtain the crystal form B.

11. A pharmaceutical composition, comprising:

(a) the pharmaceutically acceptable salt of the compound of formula X according to claim 1; and (b) a pharmaceutically acceptable carrier.

12. A method for preventing and/or treating a MOR receptor agonist mediated related disease, comprising: administering to a subject in need thereof a therapeutically effective amount of the pharmaceutically acceptable salt of the compound of formula X according to claim 1.

13. The method according to claim 12, wherein the MOR receptor agonist mediated related disease is selected from pain, immune dysfunction, inflammation, esophageal reflux, neurological and psychiatric disease, urinary and reproductive disease, cardiovascular disease and respiratory disease.

14. The preparation method according to claim 5, wherein a molar ratio of the acid and the compound of the formula X is (1.1-1.3):1.

* * * * *